(12) United States Patent
Kurokawa et al.

(10) Patent No.: US 6,383,354 B1
(45) Date of Patent: May 7, 2002

(54) GAS CONCENTRATION SENSING APPARATUS

(75) Inventors: Eiichi Kurokawa, Okazaki; Tomoo Kawase, Nagoya; Satoshi Hada, Kariya; Toshiyuki Suzuki, Handa, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/394,030

(22) Filed: Sep. 13, 1999

(30) Foreign Application Priority Data

Sep. 16, 1998 (JP) .......................... 10-261424
Jul. 19, 1999 (JP) .......................... 11-204368

(51) Int. Cl.[7] .......................................... G01N 27/407
(52) U.S. Cl. .................. 204/425; 204/406; 204/426; 205/781
(58) Field of Search ............................ 204/424, 425, 204/426, 406; 205/781

(56) References Cited

U.S. PATENT DOCUMENTS

| | | | | |
|---|---|---|---|---|
| 4,553,424 A | * | 11/1985 | Kato et al. ................... | 204/425 |
| 4,877,511 A | * | 10/1989 | Nakajima et al. ........... | 204/406 |
| 4,915,813 A | * | 4/1990 | Nakajima et al. ........... | 204/406 |
| 5,312,538 A | * | 5/1994 | Metrich ........................ | 204/425 |
| 5,833,836 A | * | 11/1998 | Takami et al. ............... | 205/785 |
| 5,866,799 A | | 2/1999 | Kato et al. | |
| 6,010,615 A | * | 1/2000 | Kato et al. ................ | 205/784.5 |
| 6,036,841 A | * | 3/2000 | Kato et al. ................... | 205/781 |
| 6,093,294 A | * | 7/2000 | Kato et al. ................... | 204/425 |

FOREIGN PATENT DOCUMENTS

| | | |
|---|---|---|
| EP | 798555 | 10/1997 |
| EP | 0 841 562 A2 | * 5/1998 |
| JP | 8-271476 | 10/1996 |
| JP | 9-318596 | 12/1997 |

* cited by examiner

*Primary Examiner*—Robert J. Warden, Sr.
*Assistant Examiner*—Kaj K. Olsen
(74) *Attorney, Agent, or Firm*—Nixon & Vanderhye P.C.

(57) ABSTRACT

A gas concentration sensing apparatus includes a gas introducing portion for introducing a measurement gas. A first cell opposed to the gas introduction portion operates for pumping oxygen from the measurement gas in the gas introducing portion. A second cell opposed to the gas introducing portion operates for sensing a concentration in a specific component of the measurement gas from which oxygen has been pumped by the first cell. There is a reference gas chamber to which at least one of the first cell and the second cell is exposed. The one of the first cell and the second cell which is exposed to the reference gas chamber includes an electrode facing the gas introducing portion. A current flowing through the first cell is sensed. A voltage is applied to the first cell in response to the sensed current through the first cell. A current flowing through the second cell is sensed. A voltage is applied to the second cell in response to the sensed current through the second cell. A voltage at the electrode is floated from a voltage of 0 V.

18 Claims, 25 Drawing Sheets

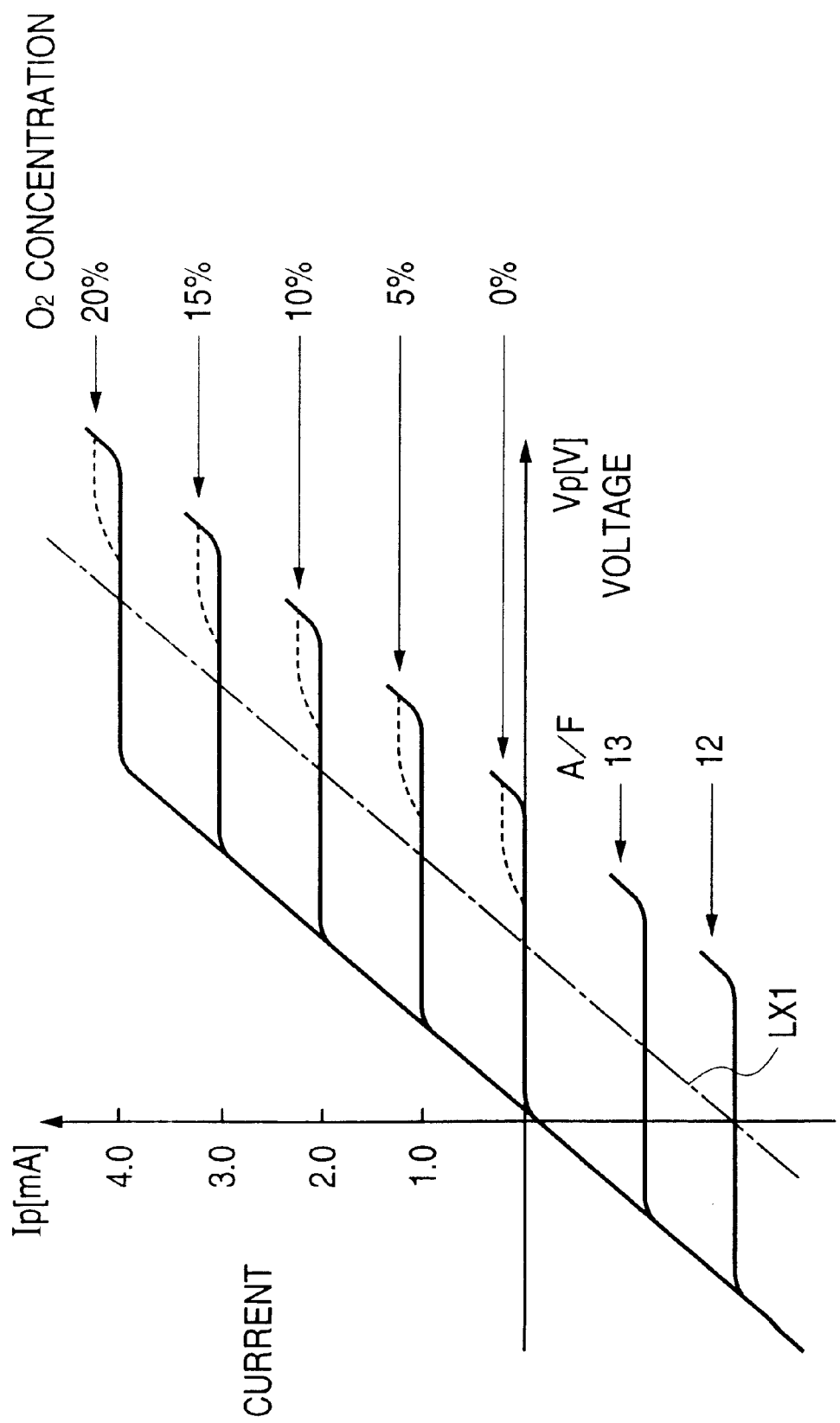

GAS CONCENTRATION SENSING APPARATUS

BACKGROUND OF THE INVENTION

1. Field of the Invention

This invention relates to a gas concentration sensing apparatus using a gas concentration sensor which detects a concentration of a specific component of a measurement gas such as an exhaust gas emitted from an automotive engine.

2. Description of the Related Art

In general, a NOx concentration sensor is necessary to implement feedback control of an automotive engine to reduce NOx emission therefrom. A NOx concentration sensor located at a point in an engine exhaust passage downstream of a NOx-processing catalytic converter can be used in a system for determining whether or not the catalytic converter has significantly deteriorated.

U.S. Pat. No. 5,866,799 corresponding to Japanese published unexamined patent application 8-271476 discloses a device for measuring a concentration of a gas component (NOx) of a measurement gas. In the device of U.S. Pat. No. 5,866,799, the measurement gas containing the gas component is introduced from an external measurement-gas space into a first internal space under a diffusion resistance. An amount of oxygen in the measurement gas within the first internal space is controlled so as to produce an atmosphere which does not substantially affect measurement of the gas component and which does not convert the gas component. The atmosphere is introduced from the first internal space into a second internal space under a diffusion resistance. Measurement is made as to the concentration of the gas component present in the atmosphere in the second internal space.

European patent application EP 0798555 A2 corresponding to Japanese published unexamined patent application 9-318596 discloses an oxide sensor (a NOx sensor) in which a measurement gas is introduced into a first chamber through a first diffusion rate-determining section, and $O_2$ is removed from the measurement gas by the aid of a pumping voltage applied between pumping electrodes. Then, the measurement gas is introduced into a second chamber through a second diffusion rate-determining section to remove excessive $O_2$ by the aid of auxiliary pumping electrodes. A detecting electrode is arranged to satisfy "$d \geq t$" provided that "d" represents a distance from an end of the auxiliary pumping electrodes on the side of the second diffusion rate-determining section to an end of the detecting electrode on the side of the second diffusion rate-determining section, and "t" represents a height of the second chamber. A predetermined pumping voltage is applied to the detecting electrode to decompose oxides contained in the measurement gas by the aid of the detecting electrode or a catalyst. The amount of oxygen produced by the decomposition is measured to determine the concentration of the oxides.

It is desirable that NOx concentration sensing apparatuses used in exhaust systems of engines to detect the NOx concentrations in exhaust gases and also the air-to-fuel ratios of air-fuel mixtures have wide sensible ranges of the air-to-fuel ratios. Also, it is desirable that the NOx concentration sensing apparatuses have good response characteristics.

SUMMARY OF THE INVENTION

It is an object of this invention to provide a gas concentration sensing apparatus which has a wide sensible range and a good response characteristic.

A first aspect of this invention provides a gas concentration sensing apparatus comprising a gas introducing portion for introducing a measurement gas; a first cell opposed to the gas introduction portion for pumping oxygen from the measurement gas in the gas introducing portion; a second cell opposed to the gas introducing portion for sensing a concentration in a specific component of the measurement gas from which oxygen has been pumped by the first cell; a reference gas chamber to which at least one of the first cell and the second cell is exposed, wherein the one of the first cell and the second cell which is exposed to the reference gas chamber includes an electrode facing the gas introducing portion; means for sensing a current flowing through the first cell; means for applying a voltage to the first cell in response to the sensed current through the first cell; means for sensing a current flowing through the second cell; means for applying a voltage to the second cell in response to the sensed current through the second cell; and means for floating a voltage at the electrode from a voltage of 0 V.

A second aspect of this invention provides a gas concentration sensing apparatus comprising a gas introducing portion for introducing a measurement gas; a first cell opposed to the gas introduction portion for pumping oxygen from the measurement gas in the gas introducing portion, the first cell including a positive-side electrode and a negative-side electrode; a second cell opposed to the gas introducing portion for sensing a concentration in a specific component of the measurement gas from which oxygen has been pumped by the first cell, the second cell including a positive-side electrode and a negative-side electrode; means for sensing a current flowing through the first cell; means for applying a voltage to the first cell in response to the sensed current through the first cell; means for sensing a current flowing through the second cell; means for applying a voltage to the second cell in response to the sensed current through the second cell; and means for floating a voltage at the negative-side electrode of the first cell and a voltage at the negative-side electrode of the second cell from a voltage of 0 V.

A third aspect of this invention is based on the first aspect thereof, and provides a gas concentration sensing apparatus wherein the floating means comprises means for applying a predetermined reference voltage to the electrode, the predetermined reference voltage being higher than the voltages which are applied to the first cell and the second cell when the measurement gas lacks oxygen.

A fourth aspect of this invention is based on the first aspect thereof, and provides a gas concentration sensing apparatus further comprising a single power supply, and means for deriving the voltages applied to the first cell and the second cell from the single power supply.

A fifth aspect of this invention is based on the first aspect thereof, and provides a gas concentration sensing apparatus further comprising an automotive battery, and means for deriving the voltages applied to the first cell and the second cell from the automotive battery, the measurement gas including an automotive exhaust gas.

A sixth aspect of this invention is based on the first aspect thereof, and provides a gas concentration sensing apparatus further comprising means for detecting an impedance of the first cell, and means for detecting an impedance of the second cell.

A seventh aspect of this invention is based on the first aspect thereof, and provides a gas concentration sensing apparatus wherein the means for sensing the current through the first cell includes a first current sensing resistor, and means for detecting a voltage across the first current sensing resistor, and wherein the means for sensing the current through the second cell includes a second current sensing resistor, and means for detecting a voltage across the second current sensing resistor.

An eighth aspect of this invention is based on the first aspect thereof, and provides a gas concentration sensing apparatus wherein the measurement gas includes an exhaust gas, and further comprising means for controlling the voltage applied to the other of the first cell and the second cell which is not exposed to the reference gas chamber to suspend transfer of oxygen via the other of the first cell and the second cell when the exhaust gas is caused by a rich air-fuel mixture.

A ninth aspect of this invention is based on the first aspect thereof, and provides a gas concentration sensing apparatus wherein the measurement gas includes an exhaust gas, and further comprising a switch circuit interposed in a voltage feed path to the other of the first cell and the second cell which is not exposed to the reference gas chamber, and means for opening the switch circuit to suspend transfer of oxygen via the other of the first cell and the second cell when the exhaust gas is caused by a rich air-fuel mixture.

A tenth aspect of this invention provides a gas concentration sensing apparatus comprising a first cell for pumping $O_2$ from a first exhaust gas to change the first exhaust gas to a second exhaust gas; a second cell for decomposing NOx in the second exhaust gas and thereby generating new $O_2$, and for pumping the new $O_2$ from the second exhaust gas to a reference gas; means for applying a voltage across the second cell; and means for changing a polarity of the voltage between a positive state and a negative state.

An eleventh aspect of this invention provides a gas concentration sensing apparatus comprising a first cell for pumping $O_2$ from a first exhaust gas to a reference gas to change the first exhaust gas to a second exhaust gas; a second cell for decomposing NOx in the second exhaust gas and thereby generating new $O_2$, and for pumping the new $O_2$ from the second exhaust gas; means for applying a voltage across the first cell; and means for changing a polarity of the voltage between a positive state and a negative state.

BRIEF DESCRIPTION OF THE DRAWINGS

FIG. 13 is a diagram of voltage-current characteristics of a pump cell in the gas concentration sensor of FIG. 12.

DESCRIPTION OF THE PREFERRED EMBODIMENTS

Figure 1:
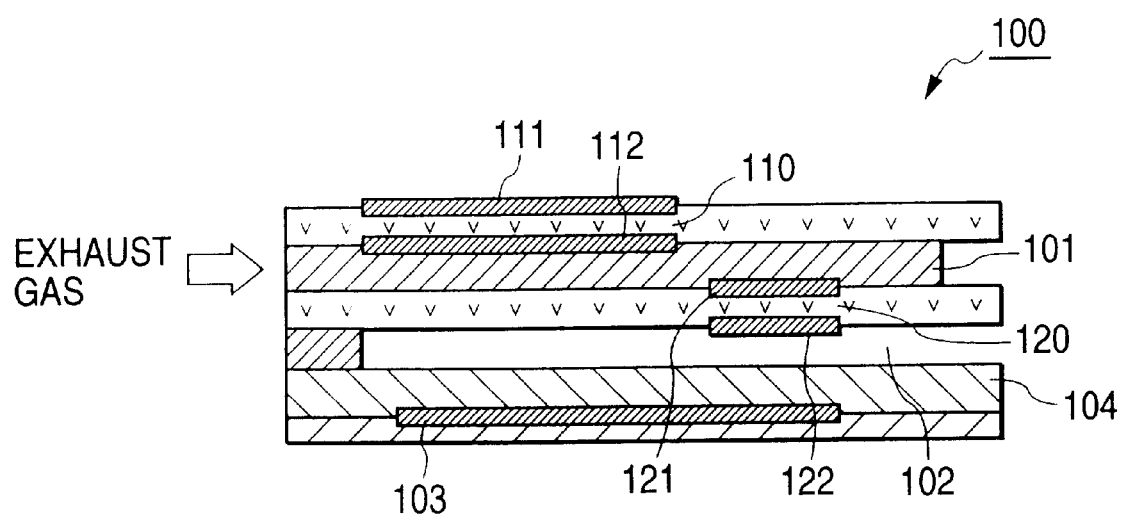
FIG. 1 is a sectional view of a comparative gas concentration sensor.

A comparative gas concentration sensor will be explained below for a better understanding of this invention. FIG. 1 shows a comparative gas concentration sensor 100 of a composite type which is designed to detect both a NOx concentration and an $O_2$ concentration. The gas concentration sensor 100 in FIG. 1 is not prior art against this invention. The gas concentration sensor 100 in FIG. 1 has two cells, that is, a pump cell for sensing an $O_2$ concentration and a sensor cell for sensing a NOx concentration.

With reference to FIG. 1, the gas concentration sensor 100 has a laminated structure including a pump cell 110, a porous diffusion layer 101, a sensor cell 120, an atmosphere duct 102, and a heater 103. The sensor 100 is connected to an engine exhaust pipe so that an upper surface, a lower surface, and a left-hand surface thereof will be exposed to an exhaust gas emitted from engine combustion chambers.

The pump cell 110 extends between the porous diffusion layer 101 and an external space filled with the exhaust gas. The exhaust-gas side or the upper side of the pump cell 110 has a first electrode 111. The diffusion-layer side or the lower side of the pump cell 110 has a second electrode 112. The sensor cell 120 extends between the porous diffusion layer 101 and the atmosphere duct 102. The diffusion-layer side or the upper side of the sensor cell 120 has a first electrode 121. The atmosphere-duct side or the lower side of the sensor cell 120 has a second electrode 122. The exhaust gas flows through the porous diffusion layer 101 along the rightward direction as viewed in FIG. 1.

Each of the pump cell 110 and the sensor cell 120 has a solid electrolytic layer made of an oxygen-ion-conductive burned oxide (ceramic). The oxygen-ion-conductive burned oxide contains $ZrO_2$, $HfO_2$, $ThO_2$, or $Bi_2O_3$ into which CaO, MgO, $Y_2O_3$, or $Yb_2O_3$ is introduced as a stabilizer by a solution treatment. The porous diffusion layer 101 is made of heat-resisting inorganic material such as alumina, magnesia, quartzite, spinel, or mullite.

The first electrode 111 of the pump cell 110, and the first and second electrodes 121 and 122 of the sensor cell 120 are made of noble metal such as Pt which has a high catalytic activity. The second electrode 112 of the pump cell 110 is made of noble metal or a noble metal alloy such as Au—Pt which is inactive to NOx, that is, which does not decompose NOx.

The heater 103 is buried in an insulating layer 104. The atmosphere duct 102 is defined between the insulating layer 104 and the sensor cell 120. An atmosphere is introduced into the atmosphere duct 102 from an external. The atmosphere in the atmosphere duct 102 is used as a reference gas for providing a reference oxygen ($O_2$) partial pressure or a reference regarding an oxygen ($O_2$) concentration. The insulating layer 104 is made of, for example, alumina. The heater 103 is made of a platinum-alumina cermet or another cermet. The heater 103 generates heat when being fed with electric power from an external. The heat generated by the heater 103 makes active the whole sensor including the pump cell 110 and the sensor cell 120.

Figure 2:
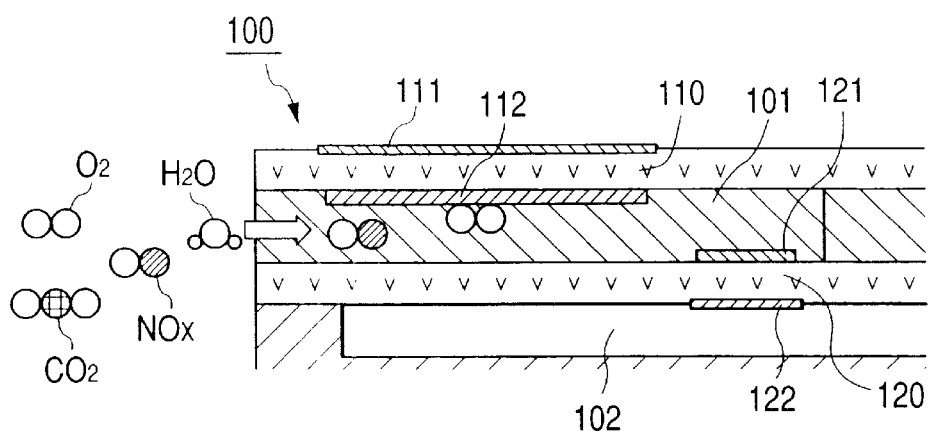
FIGS. 2, 3, and 4 are sectional views of a portion of the gas concentration sensor in FIG. 1.

The gas concentration sensor 100 in FIG. 1 operates as follows. With reference to FIG. 2, an exhaust gas enters the porous diffusion layer 101 via the left-hand end surface thereof. In general, the exhaust gas contains gas components such as oxygen ($O_2$), nitrogen oxides (NOx), carbon dioxide ($CO_2$), and water ($H_2O$). The exhaust gas flows rightward in the porous diffusion layer 101. A voltage is applied to the pump cell 110. A specific component of the exhaust gas is pumped out by the voltage application to the pump cell 110.

Figure 3:
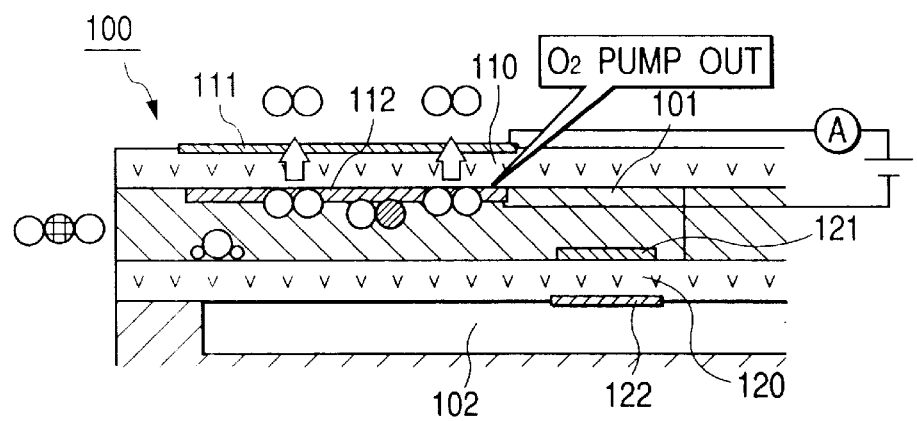

As previously mentioned, the second electrode 112 of the pump cell 110 is inactive to NOx. Therefore, as shown in FIG. 3, only oxygen ($O_2$) is pumped from the exhaust gas in the porous diffusion layer 101. The oxygen ($O_2$) is drawn into the pump cell 110 from the porous diffusion layer 101, being transferred through the pump cell 110 before being discharged via the first pump electrode 111 into the exhaust gas in the external space, that is, the exhaust gas surrounding the body of the sensor 100. At this time, an electric current which flows through the pump cell 110 is detected as an indication of the oxygen ($O_2$) concentration in the exhaust gas.

Figure 4:
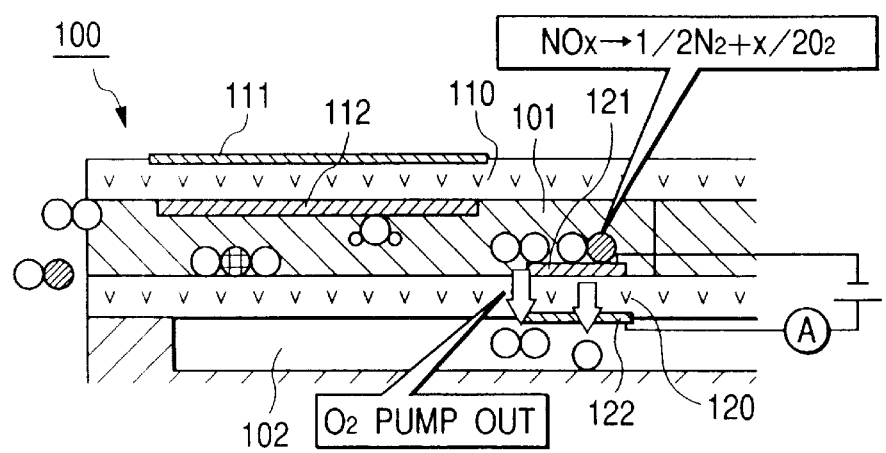

The pump cell 110 separates only a portion of the oxygen ($O_2$) component from the exhaust gas in the porous diffusion layer 101. Therefore, the exhaust gas which contains a remaining portion of the oxygen ($O_2$) component flows from the region near the pump cell 110 to a region in the porous diffusion layer 101 near the sensor cell 120. A voltage is applied to the sensor cell 120. As shown in FIG. 4, the exhaust gas in the region near the sensor cell 120 is decomposed by the voltage application to the sensor cell 120. Specifically, NOx in the exhaust gas is decomposed through a reaction as "NOx→$(1/2)N_2+(x/2)O_2$". Thus, the decomposition of NOx causes new oxygen ($O_2$). The remaining oxygen ($O_2$) and the new oxygen ($O_2$) are drawn into the sensor cell 120 from the porous diffusion layer 101, being transferred through the sensor cell 120 before being discharged via the second sensor electrode 122 into the atmosphere in the atmosphere duct 102. At this time, an electric current which flows through the sensor cell 120 is detected as an indication of the NOx concentration in the exhaust gas. The remaining oxygen ($O_2$) causes a decomposition current which is an offset current superimposed on the NOx-concentration-indicating electric current flowing through the sensor cell 120.

Figure 5:
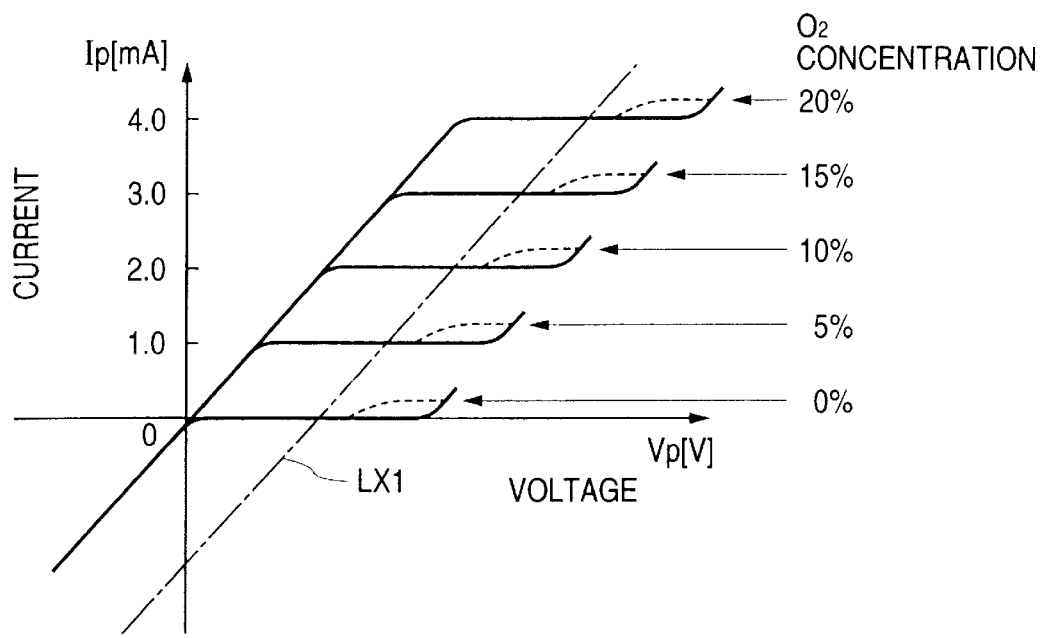
FIG. 5 is a diagram of voltage-current characteristics of a pump cell in the gas concentration sensor in FIG. 1.

The pump cell 110 has characteristics as follows. A pump cell current flowing from the first pump electrode 111 to the second pump electrode 112 is defined as being positive. On the other hand, a pump cell current flowing from the second pump electrode 112 to the first pump electrode 111 is defined as being negative. FIG. 5 shows V-I (voltage-current) characteristics of the pump cell 110. As shown in FIG. 5, a current is limited depending on the oxygen ($O_2$) concentration. In FIG. 5, "Vp" of the abscissa denotes the pump cell applied voltage (the voltage applied to the pump cell 110), and "Ip" of the ordinate denotes the pump cell current (the current flowing through the pump cell 110). The current limited range corresponds to a straight portion of each characteristic curve which is parallel to the abscissa, that is, the V-axis. The current limited range shifts toward the positive voltage side as the oxygen ($O_2$) concentration increases.

If the pump cell applied voltage is fixed at a constant level during a change in the oxygen ($O_2$) concentration, it is difficult to implement accurate detection of the oxygen ($O_2$) concentration by using the previously-mentioned limited current range (the straight portion of each characteristic curve which is parallel to the V-axis). This means that the pump cell 110 can not remove a sufficient amount of oxygen, and an amount of remaining oxygen which reaches the sensor cell 120 increases. The increased amount of remaining oxygen causes an increased error in the NOx-detecting current. Accordingly, control is implemented to apply a voltage corresponding to the angle of a dc resistance component of the pump cell 110 (the angle of a slope increasing as the applied voltage rises), that is, a voltage denoted by the line LX1 in FIG. 5. This control enables a desired sensor current (a limited current) to be provided for every value of the oxygen ($O_2$) concentration in the exhaust gas.

Since the second electrode 112 of the pump cell 110 is inactive to NOx, the pump cell 110 hardly decomposes NOx in the exhaust gas provided that the pump cell applied voltage is lower than a given level. As the pump cell applied voltage exceeds the given level, the pump cell 110 appreciably decomposes NOx in the exhaust gas. In this case, as denoted by the broken lines in FIG. 5, a pump cell current depending on the NOx concentration flows in addition to an oxygen-concentration-representing pump cell current. Thus, the applied control voltage denoted by the line LX1 in FIG. 5 is chosen so that the pump cell 110 will not appreciably decompose NOx in the exhaust gas.

Figure 6:
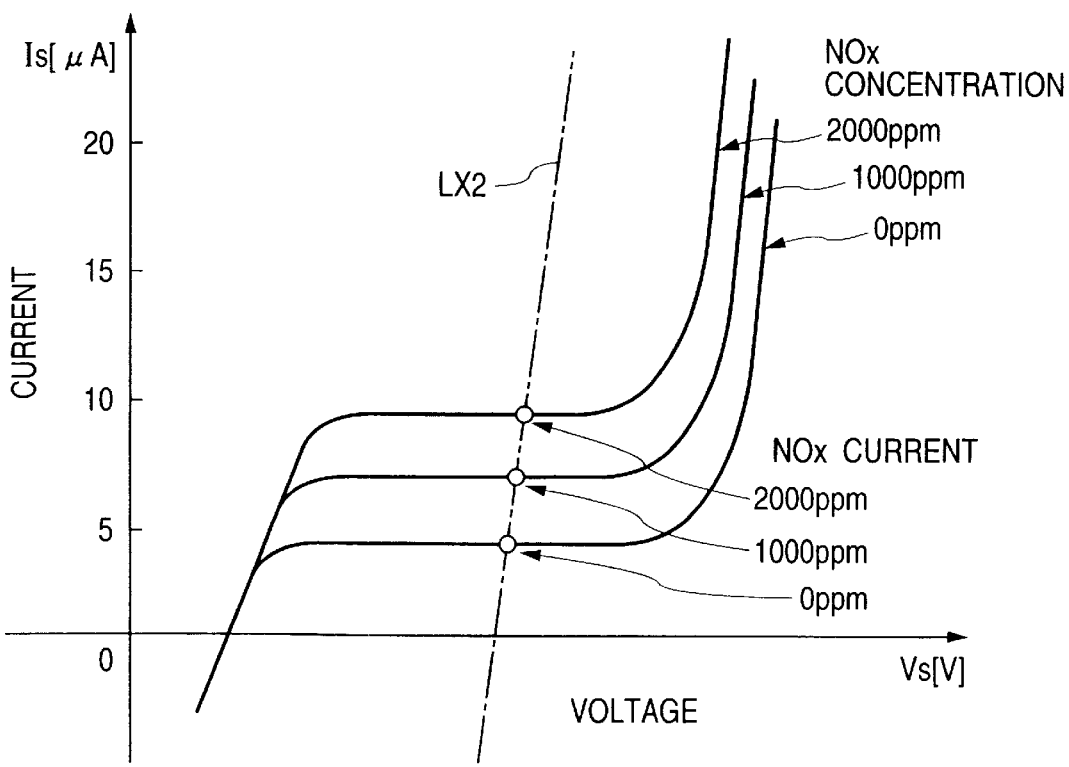
FIGS. 6 and 7 are diagrams of voltage-current characteristics of a sensor cell in the gas concentration sensor in FIG. 1.

The sensor cell 120 has characteristics as follows. A sensor cell current flowing from the first sensor electrode 121 to the second sensor electrode 122 is defined as being positive. On the other hand, a sensor cell current flowing from the second sensor electrode 122 to the first sensor electrode 121 is defined as being negative. FIG. 6 shows V-I (voltage-current) characteristics of the sensor cell 120. As shown in FIG. 6, a current is limited depending on the NOx concentration. In FIG. 6, "Vs" of the abscissa denotes the sensor cell applied voltage (the voltage applied to the sensor cell 120), and "Is" of the ordinate denotes the sensor cell current (the current flowing through the sensor cell 120). The current limited range corresponds to a straight portion of each characteristic curve which is parallel to the abscissa, that is, the V-axis. The current limited range slightly shifts toward the positive voltage side as the NOx concentration increases. The sensor cell applied voltage is controlled according to the line LX2 in FIG. 6 so that a desired sensor current (a limited current) can be provided for every value of the NOx concentration in the exhaust gas.

In the case where the exhaust gas is caused by an air-fuel mixture richer than stoichiometric and hence hardly contains $O_2$, the pump cell 110 of the gas concentration sensor 100 in FIG. 1 operates as follows. The pump cell 110 extends between the porous diffusion layer 101 and the external space occupied by the exhaust gas. Since the exhaust gas hardly contains $O_2$, the pump cell 110 does not pump $O_2$ (originally-existing $O_2$) from the external space toward the porous diffusion layer 101. In other words, a negative limited current can not flow through the pump cell 110. Thus, it is difficult to provide a negative limited current characteristic. If a positive voltage is applied to drive a current from the first pump electrode 111 to the second pump electrode 112, or if a negative voltage is applied to drive a current from the second pump electrode 112 to the first pump electrode 111, the pump cell 110 does not exhibit any limited current characteristic. In the case where the exhaust gas is caused by an air-fuel mixture richer than stoichiometric, when a negative voltage is applied to the pump cell 110, $H_2O$ and CO in the exhaust gas in the external space are decomposed so that oxygen ($O_2$) is newly generated. The new oxygen ($O_2$) is transferred from the first pump electrode 111 to the second pump electrode 112 while a corresponding current flows through the pump cell 110. In the case where the exhaust gas is caused by an air-fuel mixture richer than stoichiometric, when a positive voltage is applied to the pump cell 110, $H_2O$ and CO in the exhaust gas in the porous diffusion layer 101 are decomposed so that oxygen ($O_2$) is newly generated. The new oxygen ($O_2$) is transferred from the second pump electrode 112 to the second pump electrode 111 while a corresponding current flows through the pump cell 110.

Figure 7:
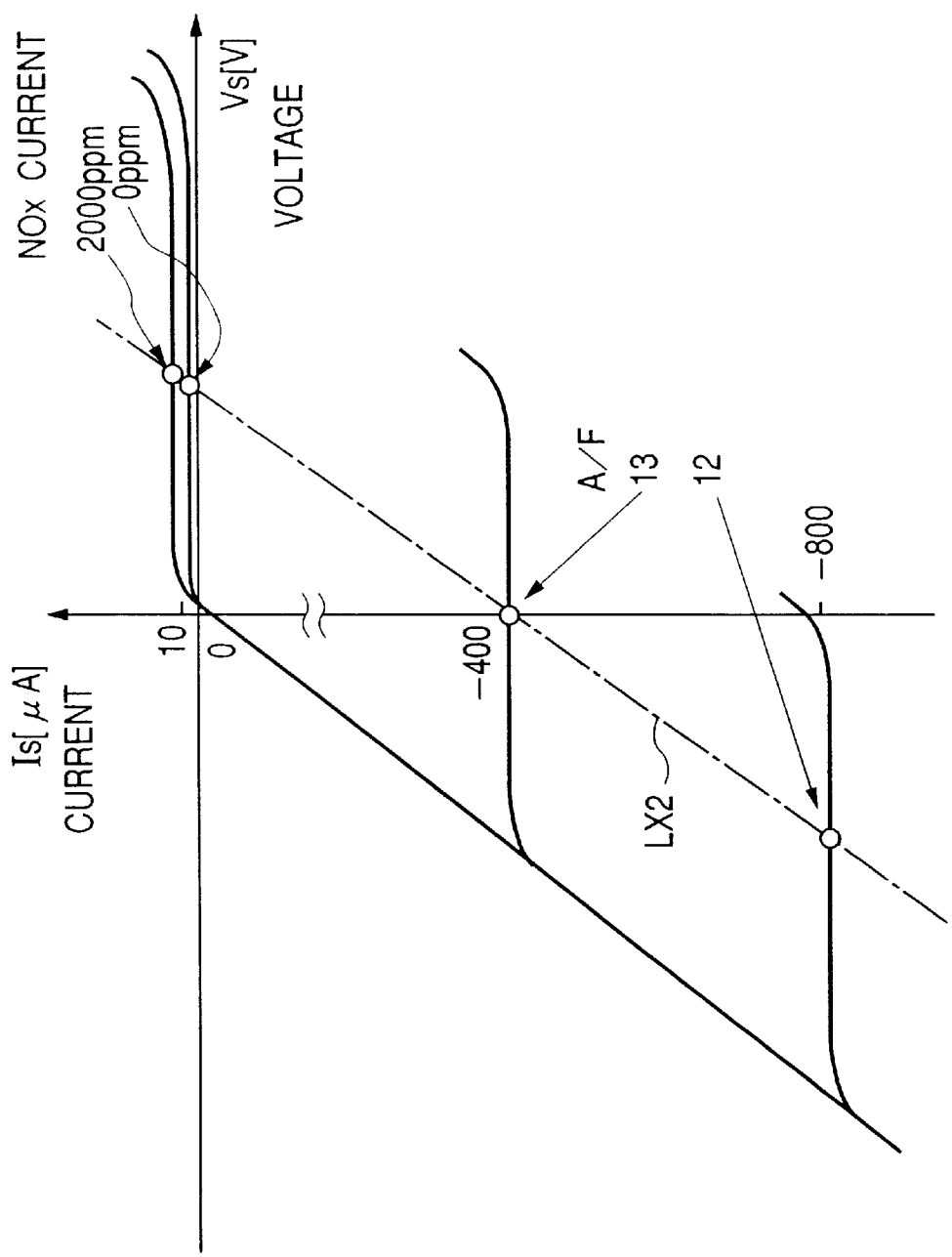

In the case where the exhaust gas is caused by an air-fuel mixture richer than stoichiometric and hence hardly contains $O_2$, the sensor cell 120 of the gas concentration sensor 100 in FIG. 1 operates as follows. The sensor cell 120 extends between the porous diffusion layer 101 and the atmosphere duct 102. Oxygen ($O_2$) can be transferred from the atmosphere duct 102 to the porous diffusion layer 101 via the second sensor electrode 122 and the first sensor electrode 121. The transfer of oxygen ($O_2$) provides a limited current characteristic. FIG. 7 shows V-I (voltage-current) characteristics of the sensor cell 120 which occur in this case. As shown in FIG. 7, a current is limited depending on the degree of the richness of an air-fuel mixture causing the exhaust gas, that is, the air-to-fuel ratio (A/F) of an air-fuel mixture causing the exhaust gas. The current levels occurring in this case are remarkably greater than the current levels which depend on the NOx concentration (for example, several tens of times, see FIG. 6).

Figure 8:
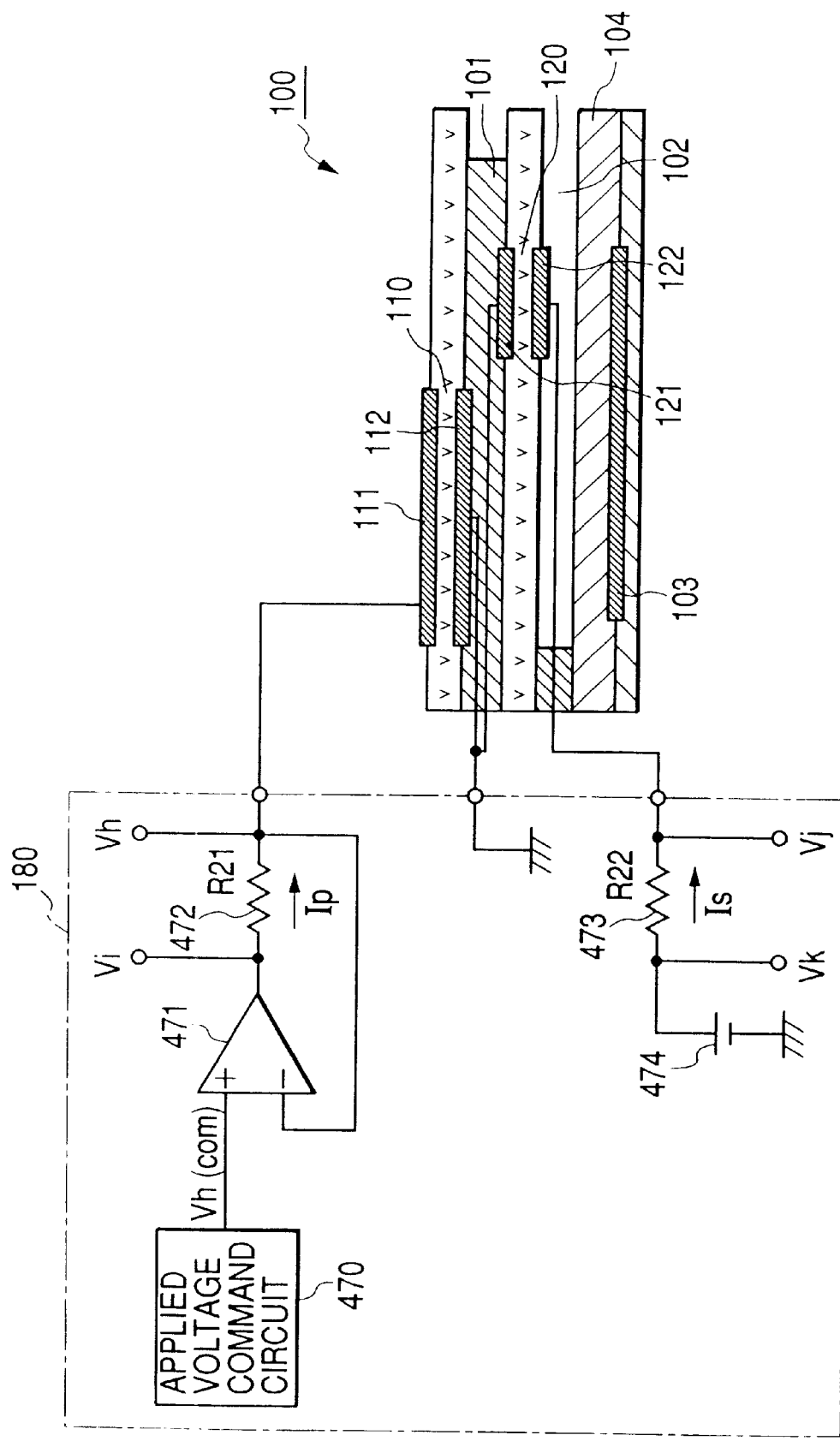
FIG. 8 is a diagram of a comparative gas concentration sensing apparatus.

FIG. 8 shows a comparative gas concentration sensing apparatus which includes the gas concentration sensor 100 and a control circuit 180 for the gas concentration sensor 100. The gas concentration sensing apparatus in FIG. 8 is not prior art against this invention. With reference to FIG. 8, the second pump electrode 112 and the first sensor electrode 121 are connected to a ground (GND) within the control circuit 180 via a common terminal. In the control circuit 180, an applied voltage command circuit 470 outputs a voltage command signal Vh(com) to the non-inverting input terminal of an amplifier circuit 471. The output terminal of the amplifier circuit 471 is connected to the first pump electrode 111 via a resistor 472. The resistor 472 acts to sense the pump cell current Ip. The voltage Vh at the first pump electrode 111 is fed back to the inverting input terminal of the amplifier circuit 470. Accordingly, the amplifier circuit 470 equalizes the voltage Vh at the first pump electrode 111 to the level of the voltage command signal Vh(com). Thus, the voltage Vh at the first pump electrode 111 is controlled in accordance with the voltage command signal Vh(com).

The pump cell current Ip which depends on the oxygen ($O_2$) concentration in the exhaust gas is expressed as follows.

$$Ip=(Vi-Vh)/R21$$

where Vi denotes the voltage at a first end of the resistor 472 which is connected to the output terminal of the amplifier circuit 471; Vh denotes the voltage at a second end of the resistor 472 which is connected to the first pump electrode 111; and R21 denotes the resistance of the resistor 472. The voltage difference (Vi–Vh) increases as the oxygen ($O_2$) concentration in the exhaust gas rises. The pump cell current Ip is detected from the voltage difference (Vi–Vh), that is, the voltage across the resistor 472. The applied voltage command circuit 470 is informed of the detected pump cell current Ip.

The applied voltage command circuit 470 sets a target applied voltage for the detected pump cell current Ip by referring to a predetermined function corresponding to the line LX1 in FIG. 5. The applied voltage command circuit 470 outputs the target applied voltage as the voltage command signal Vh(com).

The second sensor electrode 122 is connected to the positive terminal of a dc power source 474 via a resistor 473. The negative terminal of the dc power source 474 is grounded. The resistor 473 acts to sense the sensor cell current Is which depends on the NOx concentration in the exhaust gas. The sensor cell current Is is expressed as follows.

$$Is=(Vk-Vj)/R22$$

where Vk denotes the voltage at a first end of the resistor 473 which is connected to the positive terminal of the dc power source 474; Vj denotes the voltage at a second end of the resistor 473 which is connected to the second sensor electrode 122; and R22 denotes the resistance of the resistor 473. The sensor cell current is detected from the voltage difference (Vk–Vj), that is, the voltage across the resistor 473.

Generally, an air-fuel mixture supplied to the engine combustion chambers varies between a lean state to a rich state in accordance with engine operating conditions. In the case where the exhaust gas is caused by an air-fuel mixture leaner than stoichiometric and hence excessively contains $O_2$, positive limited currents flow through the pump cell 110 and the sensor cell 120 respectively. In the case where the exhaust gas is caused by an air-fuel mixture richer than stoichiometric and hence hardly contains$O_2$, a negative limited current can flow through the sensor cell 120. To enable such a negative limited current to actually flow, it is necessary to apply a suitable negative voltage to the sensor cell 120. Since the first electrode 121 of the sensor cell 120 which normally forms a negative-side electrode is grounded, it is difficult to apply a negative voltage to the sensor cell 120. Thus, it is also difficult to actually drive a negative current through the sensor cell 120. In the absence of a negative current through the sensor cell 120, oxygen ($O_2$) is not fed from the atmosphere in the atmosphere duct 102 to the porous diffusion layer 101 so that the oxygen ($O_2$) concentration in the exhaust gas in the porous diffusion layer 101 moves out of the stoichiometric state. Accordingly, when the exhaust gas caused by a rich air-fuel mixture is replaced by the exhaust gas originating from a lean air-fuel mixture, it takes a long time for the oxygen ($O_2$) concentration in the exhaust gas in the porous diffusion layer 101 to return to the stoichiometric state. During such a long time (for example, one second to several seconds), the gas concentration sensor 100 fails to accurately detect the oxygen ($O_2$) concentration and the NOx concentration in the exhaust gas.

As understood from the previous explanation, the gas concentration sensing apparatus in FIG. 8 tends to be narrow in sensible range of the air-to-fuel ratio (A/F) of an air-fuel mixture causing the exhaust gas. Also, the gas concentration sensing apparatus in FIG. 8 tends to be insufficient in response characteristic.

First Embodiment

A first embodiment of this invention is directed to a gas concentration sensing apparatus applied to an air-to-fuel ratio control system for an automotive engine. The air-to-fuel ratio control system adjusts the rate of fuel injection into the engine in response to the results of the detection by the gas concentration sensing apparatus to feedback-control the air-fuel ratio of an air-fuel mixture at a desired ratio. The gas concentration sensing apparatus is of a composite type which is designed to detect both a NOx concentration and an $O_2$ concentration in an exhaust gas emitted from the combustion chambers of the engine.

Specifically, the air-fuel ratio of an air-fuel mixture supplied to the combustion chambers of the engine is feedback-controlled in response to the $O_2$ concentration detected by the gas concentration sensing apparatus. A NOx catalytic converter (for example, a catalytic converter for absorbing and reducing NOx) is connected to an engine exhaust pipe. The NOx sensing portion of the gas concentration sensing apparatus is connected to a region of the engine exhaust pipe downstream of the NOx catalytic converter. The amount of NOx in the exhaust gas downstream of the NOx catalytic converter, that is, the amount of NOx passing through the NOx catalytic converter without being processed thereby, is calculated from the NOx concentration detected by the gas concentration sensing apparatus. When the calculated NOx amount increases above a reference level, a process of recovering the performance of the NOx catalytic converter is executed. The recovering process includes a step of supplying a rich air-fuel mixture to the engine to expose the NOx catalytic converter to an exhaust gas originating from the rich air-fuel mixture. The exposure of the NOx catalytic converter to such an exhaust gas removes absorbed ions from the NOx catalytic converter.

Figure 9:
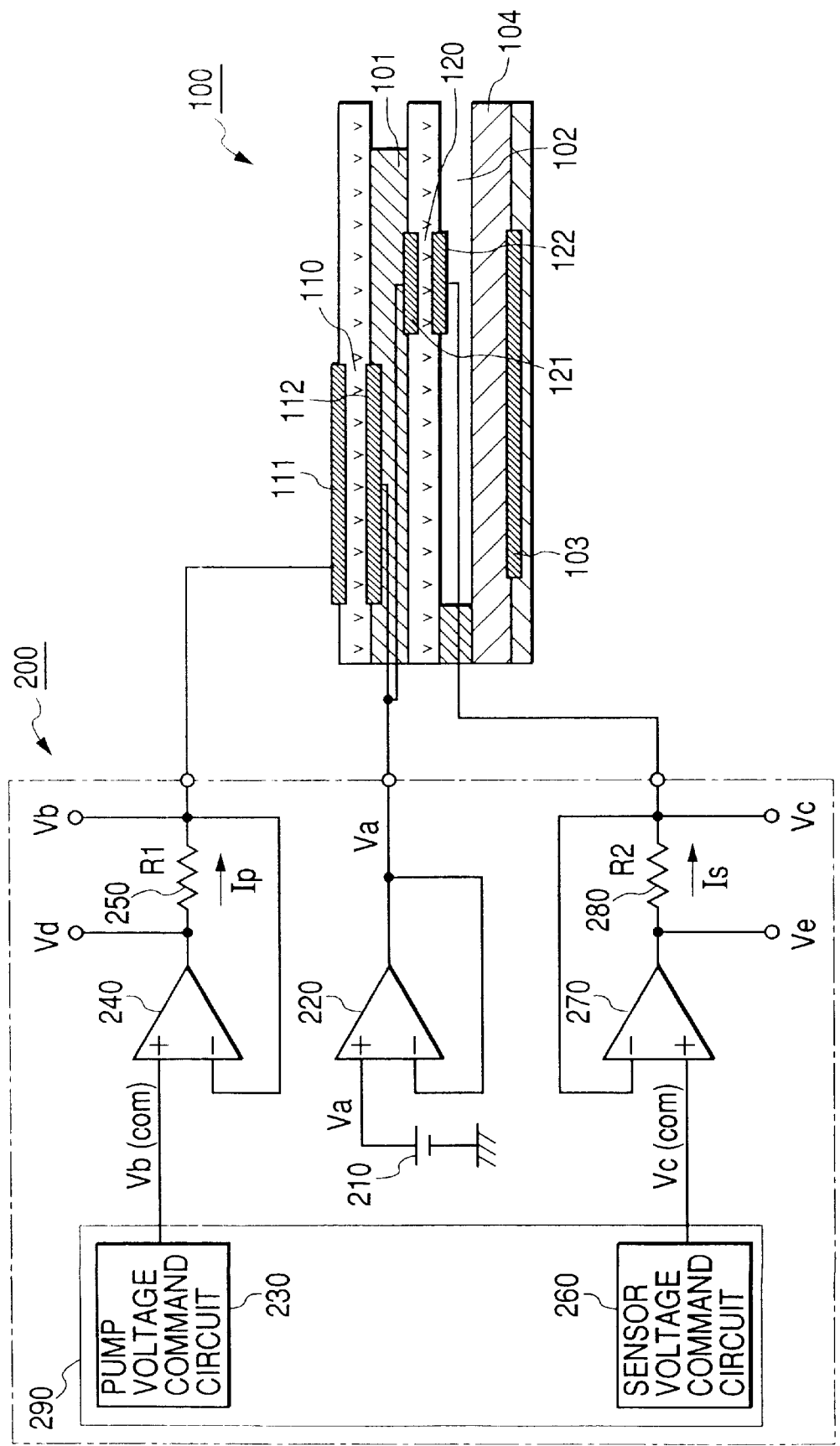
FIG. 9 is a diagram of a gas concentration sensing apparatus according to a first embodiment of this invention.

FIG. 9 shows the gas concentration sensing apparatus according to the first embodiment of this invention. The gas concentration sensing apparatus in FIG. 9 includes a gas concentration sensor 100 and a control circuit 200 which are connected to each other. Voltages derived from the voltage (12 V or 24 V) across an automotive battery are applied to the gas concentration sensor 100.

With reference to FIG. 9, the gas concentration sensor 100 has a laminated structure including a pump cell 110, a porous diffusion layer 101, a sensor cell 120, an atmosphere duct 102, and a heater 103. The sensor 100 is connected to an engine exhaust pipe so that an upper surface, a lower surface, and a left-hand surface thereof will be exposed to an exhaust gas emitted from engine combustion chambers.

The pump cell 110 extends between the porous diffusion layer 101 and an external space filled with the exhaust gas. The exhaust-gas side or the upper side of the pump cell 110 has a first electrode 111. The diffusion-layer side or the lower side of the pump cell 110 has a second electrode 112. The sensor cell 120 extends between the porous diffusion layer 101 and the atmosphere duct 102. The diffusion-layer side or the upper side of the sensor cell 120 has a first electrode 121. The atmosphere-duct side or the lower side of the sensor cell 120 has a second electrode 122. The exhaust gas flows through the porous diffusion layer 101 along the rightward direction as viewed in FIG. 9.

Each of the pump cell 110 and the sensor cell 120 has a solid electrolytic layer made of an oxygen-ion-conductive burned oxide (ceramic). The oxygen-ion-conductive burned oxide contains $ZrO_2$, $HfO_2$, $ThO_2$, or $Bi_2O_3$ into which $CaO$, $MgO$, $Y_2O_3$, or $Yb_2O_3$ is introduced as a stabilizer by a solution treatment. In the pump cell 110, the solid electrolytic layer is sandwiched between the first electrode 111 and the second electrode 112. In the sensor cell 120, the solid electrolytic layer is sandwiched between the first electrode 121 and the second electrode 122. The porous diffusion layer 101 is made of heat-resisting inorganic material such as alumina, magnesia, quartzite, spinel, or mullite.

The first electrode 111 of the pump cell 110, and the first and second electrodes 121 and 122 of the sensor cell 120 are made of noble metal such as Pt which has a high catalytic activity. The second electrode 112 of the pump cell 110 is made of noble metal or a noble metal alloy such as Au—Pt which is inactive to NOx, that is, which does not decompose NOx.

The heater 103 is buried in an insulating layer 104. The atmosphere duct 102 is defined between the insulating layer 104 and the sensor cell 120. The atmosphere duct 102 forms a reference gas chamber. An atmosphere is introduced into the atmosphere duct 102 from an external. The atmosphere in the atmosphere duct 102 is used as a reference gas for providing a reference oxygen ($O_2$) partial pressure or a reference regarding an oxygen ($O_2$) concentration. The insulating layer 104 is made of, for example, alumina. The heater 103 is made of a platinum-alumina cermet or another cermet. The heater 103 generates heat when being fed with electric power from an external. The heat generated by the heater 103 makes active the whole sensor including the pump cell 110 and the sensor cell 120.

The gas concentration sensor 100 in FIG. 9 operates as follows. An exhaust gas enters the porous diffusion layer 101 via the left-hand end surface thereof. In general, the exhaust gas contains gas components such as oxygen ($O_2$), nitrogen oxides (NOx), carbon dioxide ($CO_2$), and water ($H_2O$). The exhaust gas flows rightward in the porous diffusion layer 101. A voltage is applied to the pump cell 110. A specific component of the exhaust gas is pumped out by the voltage application to the pump cell 110.

As previously mentioned, the second electrode 112 of the pump cell 110 is inactive to NOx. Therefore, only oxygen ($O_2$) is pumped from the exhaust gas in the porous diffusion layer 101. The oxygen ($O_2$) is drawn into the pump cell 110 from the porous diffusion layer 101, being transferred through the pump cell 110 before being discharged via the first pump electrode 111 into the exhaust gas in the external space, that is, the exhaust gas surrounding the body of the sensor 100. At this time, an electric current which flows through the pump cell 110 is detected as an indication of the oxygen ($O_2$) concentration in the exhaust gas.

The pump cell 110 separates only a portion of the oxygen ($O_2$) component from the exhaust gas in the porous diffusion layer 101. Therefore, the exhaust gas which contains a remaining portion of the oxygen ($O_2$) component flows from the region near the pump cell 110 to a region in the porous diffusion layer 101 near the sensor cell 120. A voltage is applied to the sensor cell 120. The exhaust gas in the region near the sensor cell 120 is decomposed by the voltage application to the sensor cell 120. Specifically, NOx in the exhaust gas is decomposed through a reaction as "NOx→(1/2)$N_2$+(x/2)$O_2$". Thus, the decomposition of NOx causes new oxygen ($O_2$). The remaining oxygen ($O_2$) and the new oxygen ($O_2$) are drawn into the sensor cell 120 from the porous diffusion layer 101, being transferred through the sensor cell 120 before being discharged via the second sensor electrode 122 into the atmosphere in the atmosphere duct 102. At this time, an electric current which flows through the sensor cell 120 is detected as an indication of the NOx concentration in the exhaust gas. The remaining oxygen ($O_2$) causes a decomposition current which is an offset current superimposed on the NOx-concentration-indicating electric current flowing through the sensor cell 120.

The pump cell 110 has a positive-side terminal and a negative-side terminal. The positive-side terminal of the pump cell 110 is connected to the first pump electrode 111. The negative-side terminal of the pump cell is connected to the second pump electrode 112. The sensor cell 120 has a positive-side terminal and a negative-side terminal. The positive-side terminal of the sensor cell 120 is connected to the second sensor electrode 122. The negative-side terminal of the sensor cell 120 is connected to the first sensor electrode 121.

As shown in FIG. 9, the control circuit 200 includes a reference voltage circuit 210 and an amplifier circuit 220. The reference voltage circuit 210 generates a predetermined reference voltage Va higher than a ground potential. The positive terminal of the reference voltage circuit 210 is connected to the non-inverting input terminal of the amplifier circuit 220. The negative terminal of the reference voltage circuit 210 is grounded. The reference voltage Va is applied to the non-inverting input terminal of the amplifier circuit 220. The output terminal of the amplifier circuit 220 is connected to the second electrode 112 of the pump cell 110 and the first electrode 121 of the sensor cell 120. The output terminal of the amplifier circuit 220 is also connected to the inverting input terminal thereof. The amplifier circuit 220 acts as a voltage follower, and hence equalizes the voltage at the second pump electrode 112 and the first sensor electrode 121 to the reference voltage Va. In other words, the reference voltage Va which is higher than the ground potential is applied to the second pump electrode 112 and the first sensor electrode 121.

The control circuit 200 also includes an applied voltage command circuit 290 having a pump voltage command circuit 230 and a sensor voltage command circuit 260. As will be made clear later, the pump voltage command circuit 230 is informed of a detected pump cell current Ip. The pump voltage command circuit 230 outputs a pump command voltage Vb(com) in response to the detected pump cell current Ip according to a predetermined function corresponding to the line LX1 in FIG. 5. The command voltage Vb(com) is designed to control the voltage applied to the pump cell 110. As will be made clear later, the sensor voltage command circuit 260 is informed of a detected sensor cell current Is. The sensor voltage command circuit 260 outputs a sensor command voltage Vc(com) in response to the detected sensor cell current Is according to a predetermined function corresponding to the line LX2 in FIG. 6. The command voltage Vc(com) is designed to control the voltage applied to the sensor cell 120.

The command voltage Vb(com) is applied from the pump voltage command circuit 230 to the non-inverting input terminal of an amplifier circuit 240. The output terminal of the amplifier circuit 240 is connected to one end of a current sensing resistor 250. The other end of the resistor 250 is connected to the first pump electrode 111 and the inverting input terminal of the amplifier circuit 240. The resistor 250 acts to sense the pump cell current Ip. The voltage Vb at the first pump electrode 111 is fed back to the inverting input terminal of the amplifier circuit 240. Accordingly, the amplifier circuit 240 equalizes the voltage Vb at the first pump electrode 111 to the command voltage Vb(com). Thus, the voltage Vb at the first pump electrode 111 is controlled at a level equal to the command voltage Vb(com).

The pump cell applied voltage (the voltage applied to the pump cell 110) Vp is expressed as follows.

$$Vp=Vb-Va$$

The pump cell current Ip which depends on the oxygen ($O_2$) concentration in the exhaust gas is expressed as follows.

$$Ip=(Vd-Vb)/R1$$

where Vd denotes the voltage at the junction between the resistor 250 and the output terminal of the amplifier circuit 240, and R1 denotes the resistance of the resistor 250. The voltage difference (Vd−Vb) is equal to the voltage across the resistor 250. The voltage difference (Vd−Vb) increases as the oxygen ($O_2$) concentration in the exhaust gas rises. The pump cell current Ip is detected from the voltage difference (Vd−Vb), that is, the voltage across the resistor 250. The pump voltage command circuit 230 is informed of the detected pump cell current Ip.

The command voltage Vc(com) is applied from the sensor voltage command circuit 260 to the non-inverting input terminal of an amplifier circuit 270. The output terminal of the amplifier circuit 270 is connected to one end of a current sensing resistor 280. The other end of the resistor 280 is connected to the second sensor electrode 122 and the inverting input terminal of the amplifier circuit 270. The resistor 280 acts to sense the sensor cell current Is. The voltage Vc at the second sensor electrode 122 is fed back to the inverting input terminal of the amplifier circuit 270. Accordingly, the amplifier circuit 270 equalizes the voltage Vc at the second sensor electrode 122 to the command voltage Vc(com). Thus, the voltage Vc at the second sensor electrode 122 is controlled at a level equal to the command voltage Vc (com).

The sensor cell applied voltage (the voltage applied to the sensor cell 120) Vs is expressed as follows.

$$Vs=Vc-Va$$

The sensor cell current Is which depends on the NOx concentration in the exhaust gas is expressed as follows.

$$Is=(Ve-Vc)/R2$$

where Ve denotes the voltage at the junction between the resistor 280 and the output terminal of the amplifier circuit 270, and R2 denotes the resistance of the resistor 280. The voltage difference (Ve−Vc) is equal to the voltage across the resistor 280. The voltage difference (Ve−Vc) varies as the NOx concentration in the exhaust gas changes. The sensor cell current Is is detected from the voltage difference (Ve−Vc), that is, the voltage across the resistor 280. The sensor voltage command circuit 260 is informed of the detected sensor cell current Is.

Figure 10:
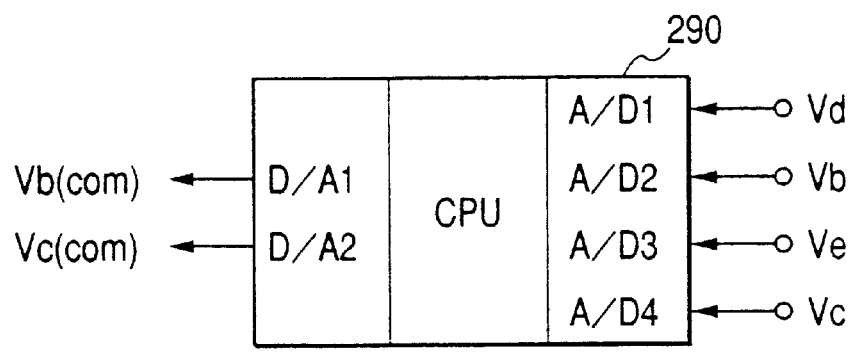
FIG. 10 is a diagram of an applied voltage command circuit in FIG. 9.

The applied voltage command circuit 290 receives the voltage Vb at the first pump electrode 111, the voltage Vd at the junction between the resistor 250 and the output terminal of the amplifier circuit 240, the voltage Vc at the second sensor electrode 122, and the voltage Ve at the junction between the resistor 280 and the output terminal of the amplifier circuit 270. As previously mentioned, the applied voltage command circuit 290 has the pump voltage command circuit 230 and the sensor voltage command circuit 260. The applied voltage command circuit 290, is formed by a microcomputer. The microcomputer includes a combination of an input port, an output port, a CPU, a RAM, and a ROM. The microcomputer operates in accordance with a control program stored in the ROM. As shown in FIG. 10, the applied voltage command circuit 290 includes analog-to-digital converters A/D1, A/D2, A/D3, and A/D4 provided in the input port. The applied voltage command circuit 290 includes digital-to-analog converters D/A1 and D/A2 provided in the output port. The analog-to-digital converter converters A/D1, A/D2, A/D3, and A/D4 receive the voltages Vd, Vb, Ve, and Vc respectively. The analog-to-digital converter A/D1 changes the voltage Vd into a corresponding digital signal handled by the CPU. The analog-to-digital converter A/D2 changes the voltage Vb into a corresponding digital signal handled by the CPU. The analog-to-digital converter A/D3 changes the voltage Ve into a corresponding digital signal handled by the CPU. The analog-to-digital converter A/D4 changes the voltage Vc into a corresponding digital signal handled by the CPU. The digital-to-analog converter D/A1 receives a digital signal representing a pump command voltage Vb(com) which is generated by the CPU. The digital-to-analog converter D/A1 changes the digital signal into the pump command voltage Vb(com), and outputs the pump command voltage Vb(com). The digital-to-analog converter D/A2 receives a digital signal representing a sensor command voltage Vc(com) which is generated by the CPU. The digital-to-analog converter D/A2 changes the digital signal into the sensor command voltage Vc(com), and outputs the sensor command voltage Vc(com).

Figure 11:
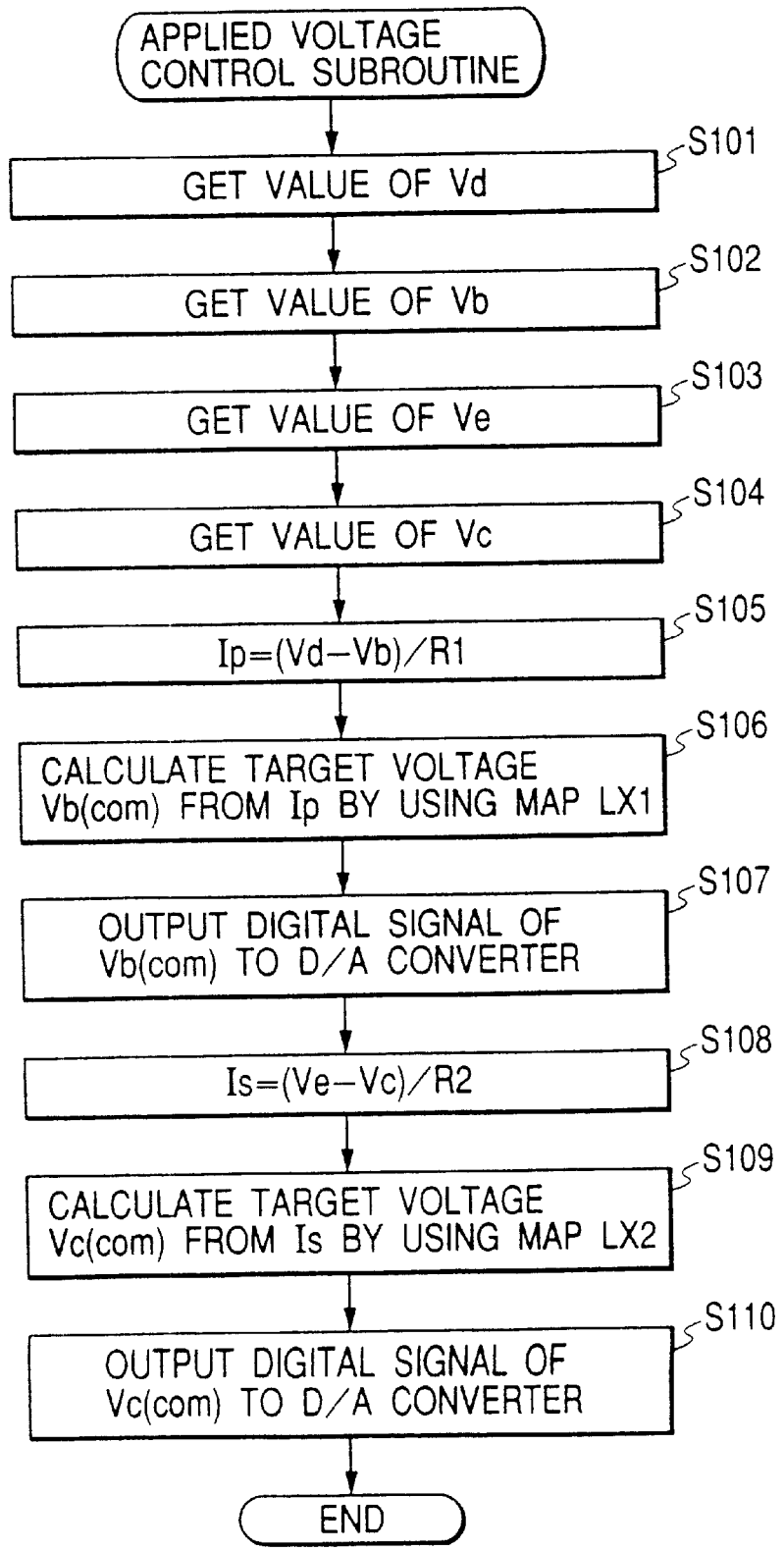
FIG. 11 is a flowchart of a subroutine of a control program for the applied voltage command circuit in FIG. 9.

FIG. 11 is a flowchart of a subroutine of the control program for the applied voltage command circuit 290. The subroutine in FIG. 11 relates to the control of applied voltages. The subroutine in FIG. 11 is periodically iterated by, for example, a timer-based interruption process during the execution of a main routine (not shown) of the control program.

As shown in FIG. 11, a first step S101 of the subroutine gets the present value of the voltage Vd from the output signal of the analog-to-digital converter A/D1. A step S102 following the step S101 gets the present value of the voltage Vb from the output signal of the analog-to-digital converter A/D2. A step S103 subsequent to the step S102 gets the present value of the voltage Ve from the output signal of the analog-to-digital converter A/D3. A step S104 following the step S103 gets the present value of the voltage Vc from the output signal of the analog-to-digital converter A/D4.

A step S105 subsequent to the step S104 calculates the pump cell current Ip from the present values of the voltages Vd and Vb, and the resistance R1 of the resistor 250 according to the equation "$Ip=(Vd-Vb)/R1$".

The ROM in the applied voltage command circuit 290 stores data of a map representing a predetermined function corresponding to the line LX1 in FIG. 5 which provides a relation between the pump cell current Ip and a target pump command voltage Vb(com). A step S106 following the step S105 calculates the target pump command voltage Vb(com) from the pump cell current Ip by referring to the related map.

A step S107 subsequent to the step S106 feeds the digital-to-analog converter D/A1 with a digital signal representing the target pump command voltage Vb(com). The digital-to-analog converter D/A1 changes the digital signal into the pump command voltage Vb(com), and outputs the pump command voltage Vb(com).

A step S108 following the step S107 calculates the sensor cell current Is from the present values of the voltages Ve and Vc, and the resistance R2 of the resistor 280 according to the equation "$Is=(Ve-Vc)/R2$".

The ROM in the applied voltage command circuit 290 stores data of a map representing a predetermined function corresponding to the line LX2 in FIG. 6 which provides a relation between the sensor cell current Is and a target sensor command voltage Vc(com). A step S109 subsequent to the step S108 calculates the target sensor command voltage Vc(com) from the sensor cell current Ip by referring to the related map.

A step S110 following the step S109 feeds the digital-to-analog converter D/A2 with a digital signal representing the target sensor command voltage Vc(com). The digital-to-analog converter D/A2 changes the digital signal into the sensor command voltage Vc(com), and outputs the sensor command voltage Vc(com). After the step S110, the current execution cycle of the subroutine ends.

As understood from the previous explanation, the pump cell current Ip is controlled according to the line LX1 in FIG. 5. The sensor cell current Is is controlled according to the line LX2 in FIG. 6. In the case of an exhaust gas originating from a rich air-to-fuel mixture, the voltage Vc at the second sensor electrode 122 is set lower than the reference voltage Va (that is, the voltage at the first sensor electrode 121) so that a negative voltage can be applied to the sensor cell 120 as shown in FIG. 7. Therefore, it is possible to detect the air-to-fuel ratio (A/F) of a rich air-fuel mixture causing the exhaust gas. In the case where the voltage Vc is set to satisfy the relation as Va>Vc>Ve or Vc>Ve, a negative sensor cell current Is is made to flow.

Since the reference voltage Va (that is, the voltage at the second pump electrode 112 and the first sensor electrode 121) is higher than the ground potential, negative currents can be made to flow through the pump cell 110 and the sensor cell 120 respectively. For not only an exhaust gas originating from a lean air-fuel mixture but also an exhaust gas originating from a rich air-fuel mixture, a gas component concentration in the exhaust gas in the porous diffusion layer 101 can be maintained at a constant level (for example, an oxygen ($O_2$) concentration in the exhaust gas in the porous diffusion layer 101 can be maintained in a stoichiometric state). Thus, it is possible to detect not only the air-to-fuel ratio (A/F) of a lean air-fuel mixture causing the exhaust gas but also the air-to-fuel ratio (A/F) of a rich air-fuel mixture causing the exhaust gas. Accordingly, a wide A/F sensible range is available. Furthermore, it is possible to provide an improved sensing response characteristic when an exhaust gas caused by a rich air-fuel mixture is replaced by an exhaust gas originating from a lean air-fuel mixture.

Second Embodiment

Figure 12:
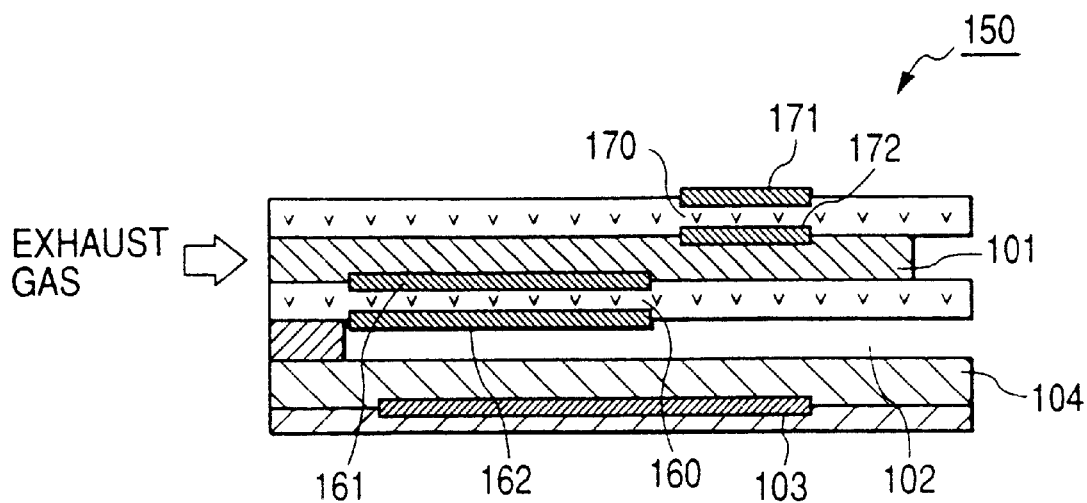
FIG. 12 is a sectional view of a gas concentration sensor in a second embodiment of this invention.

FIG. 12 shows a gas concentration sensor 150 in a second embodiment of this invention. The gas concentration sensor 150 is similar to the gas concentration sensor 100 in FIG. 9 except for design changes mentioned later.

With reference to FIG. 12, the gas concentration sensor 150 has a laminated structure including a sensor cell 170, a porous diffusion layer 101, a pump cell 160, an atmosphere duct 102, and a heater 103. The pump cell 160 acts to sense an $O_2$ concentration. The sensor cell 170 acts to sense a NOx concentration.

The pump cell 160 extends between the porous diffusion layer 101 and the atmosphere duct 102. The diffusion-layer side or the upper side of the pump cell 160 has a first electrode 161. The atmosphere-duct side or the lower side of the pump cell 160 has a second electrode 162. The sensor cell 170 extends between the porous diffusion layer 101 and an external space filled with an exhaust gas. The exhaust-gas side or the upper side of the sensor cell 170 has a first electrode 171. The diffusion-layer side or the lower side of the sensor cell 170 has a second electrode 172. The exhaust gas flows through the porous diffusion layer 101 along the rightward direction as viewed in FIG. 12.

The second electrode 161 of the pump cell 160, and the first and second electrodes 171 and 172 of the sensor cell 170 are made of noble metal such as Pt which has a high catalytic activity. The first electrode 161 of the pump cell 160 is made of noble metal or a noble metal alloy such as Au—Pt which is inactive to NOx, that is, which does not decompose NOx.

The heater 103 is buried in an insulating layer 104. The atmosphere duct 102 is defined between the insulating layer 104 and the pump cell 160.

The gas concentration sensor 150 in FIG. 12 operates as follows. In the case where the exhaust gas originates from a lean air-fuel mixture, a limited current which depends on the oxygen ($O_2$) concentration in the exhaust gas is made to flow through the pump cell 160. In addition, a limited current which depends on the NOx concentration in the exhaust gas is made to flow through the sensor cell 170. Accordingly, the oxygen ($O_2$) concentration and the NOx concentration in the exhaust gas are detected by the pump cell 160 and the sensor cell 170 respectively.

In the case where the exhaust gas is caused by an air-fuel mixture richer than stoichiometric and hence hardly contains $O_2$, the sensor cell 170 operates as follows. The sensor cell 170 extends between the porous diffusion layer 101 and the external space filled with the exhaust gas. Since the exhaust gas hardly contains $O_2$, the sensor cell 170 does not pump $O_2$ (originally-existing $O_2$) from the external space toward the porous diffusion layer 101. In other words, a negative limited current which depends on the NOx concentration in the exhaust gas can not flow through the sensor cell 170. Thus, it is difficult to provide a negative limited current characteristic related to the NOx concentration. In the case where the exhaust gas originates from a rich air-fuel mixture, when a negative voltage is applied to the sensor cell 170, $H_2O$ and CO in the exhaust gas in the external space are decomposed so that oxygen ($O_2$) is newly generated. The new oxygen ($O_2$) is transferred from the first sensor electrode 171 to the second sensor electrode 172 while a corresponding current unrelated to the NOx concentration flows through the sensor cell 170.

In the case where the exhaust gas is caused by an air-fuel mixture richer than stoichiometric and hence hardly contains $O_2$, the pump cell 160 operates as follows. The pump cell 160 extends between the porous diffusion layer 101 and the atmosphere duct 102. The pump cell 160 pumps $O_2$ from the atmosphere in the atmosphere duct 102 toward the porous diffusion layer 101. Thus, it is possible to provide a limited current characteristic related to the degree of the richness of an air-fuel mixture causing the exhaust gas, that is, the air-to-fuel ratio (A/F) of an air-fuel mixture causing the exhaust gas.

FIG. 13 shows V-I (voltage-current) characteristics of the pump cell 160. As shown in FIG. 13, a current is limited depending on the oxygen ($O_2$) concentration in the exhaust gas. In the case where the exhaust gas originates from a rich air-fuel mixture, it is preferable to apply a negative voltage to the pump cell 160 to drive a negative current therethrough which depends on the air-to-fuel ratio (A/F) of the air-fuel mixture.

Figure 14:
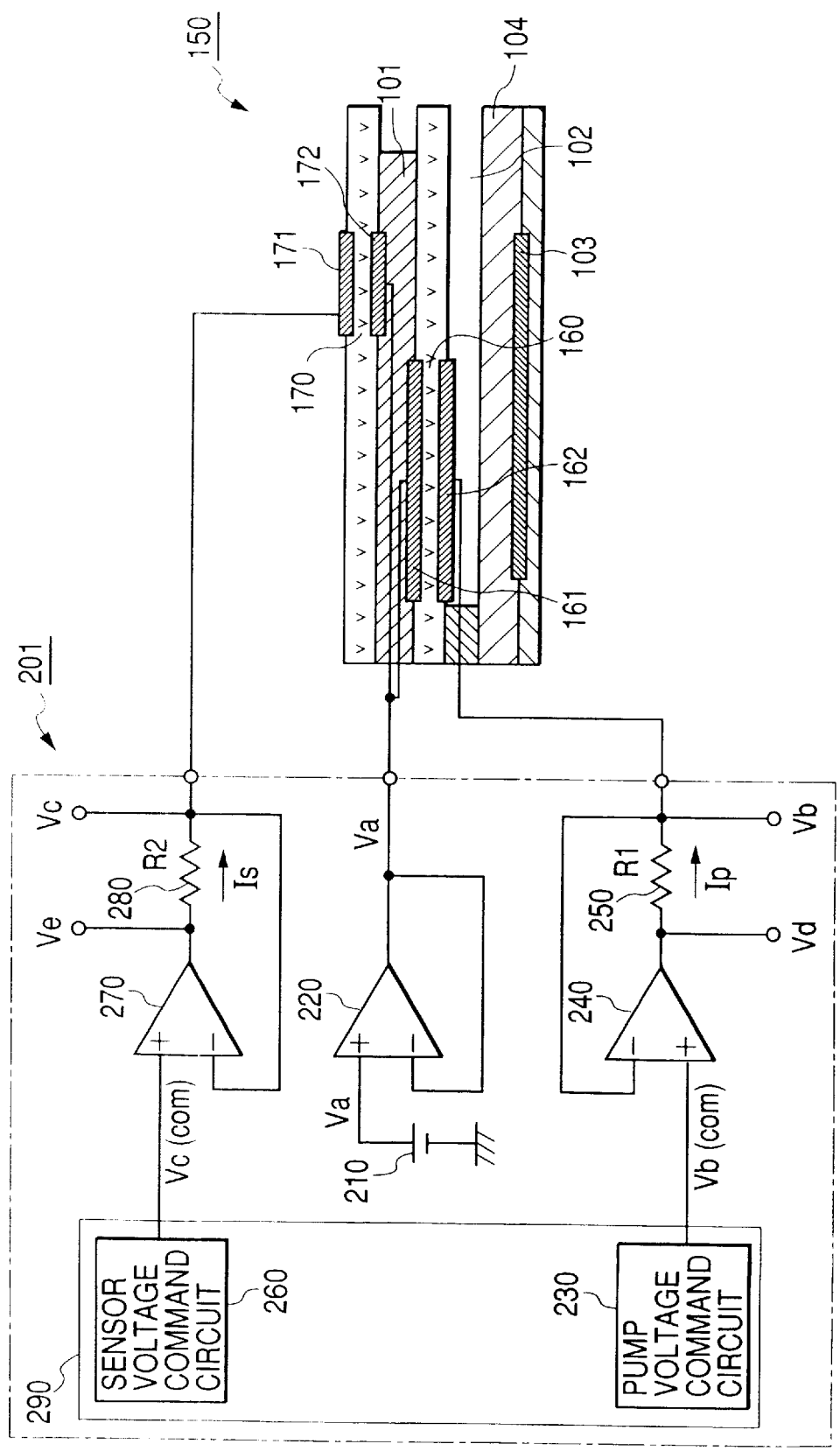
FIG. 14 is a diagram of a gas concentration sensing apparatus according to the second embodiment of this invention.

As shown in FIG. 14, the gas concentration sensor 150 is connected to a control circuit 201. The control circuit 201 is basically similar to the control circuit 200 in FIG. 9.

With reference to FIG. 14, an amplifier circuit 220 in the control circuit 201 applies a reference voltage Va to the first pump electrode 161 and the second sensor electrode 172. The reference voltage Va is higher than a ground potential. The output terminal of an amplifier circuit 240 in the control circuit 201 is connected via a current sensing resistor 250 to the second pump electrode 162. The output terminal of an amplifier circuit 270 in the control circuit 201 is connected via a current sensing resistor 280 to the first sensor electrode 171.

Since the reference voltage Va (that is, the voltage at the first pump electrode 161 and the second sensor electrode 172) is higher than the ground potential, negative currents can be made to flow through the pump cell 160 and the sensor cell 170 respectively. For not only an exhaust gas originating from a lean air-fuel mixture but also an exhaust gas originating from a rich air-fuel mixture, a gas component concentration in the exhaust gas in the porous diffusion layer 101 can be maintained at a constant level (for example, an oxygen ($O_2$) concentration in the exhaust gas in the porous diffusion layer 101 can be maintained in a stoichiometric state). Thus, it is possible to detect not only the air-to-fuel ratio (A/F) of a lean air-fuel mixture causing the exhaust gas but also the air-to-fuel ratio (A/F) of a rich air-fuel mixture causing the exhaust gas. Accordingly, a wide A/F sensible range is available. Furthermore, it is possible to provide an improved sensing response characteristic when an exhaust gas caused by a rich air-fuel mixture is replaced by an exhaust gas originating from a lean air-fuel mixture.

Third Embodiment

Figure 15:
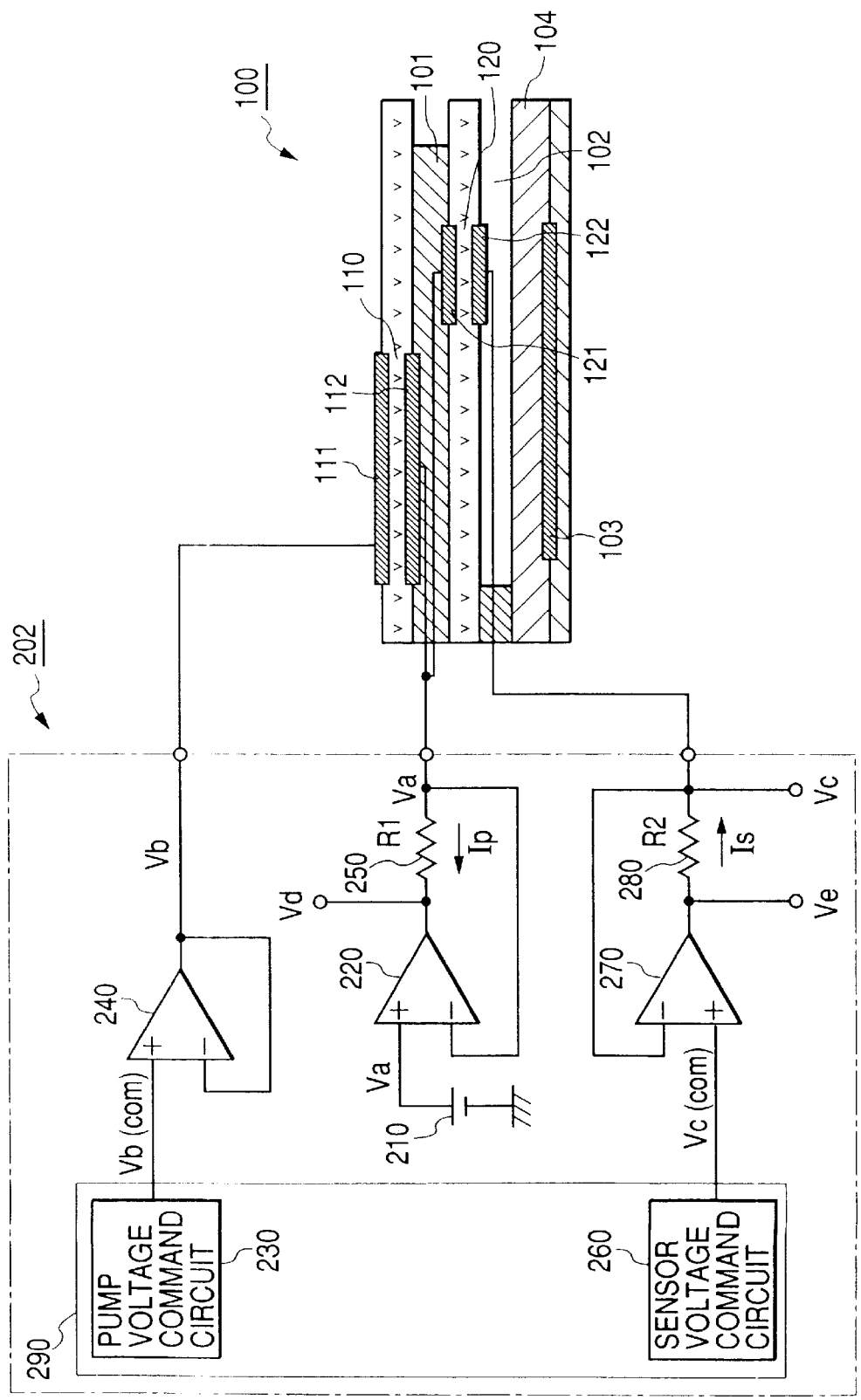
FIG. 15 is a diagram of a gas concentration sensing apparatus according to a third embodiment of this invention.

FIG. 15 shows a third embodiment of this invention which is similar to the first embodiment thereof except for design changes mentioned later. The embodiment of FIG. 15 includes a control circuit 202 which replaces the control circuit 200 in FIG. 9.

As shown in FIG. 15, the output terminal of an amplifier circuit 240 in the control circuit 202 is directly connected to a first pump electrode 111. Also, the output terminal of the amplifier circuit 240 is connected to the inverting input terminal thereof. The amplifier circuit 240 equalizes the voltage Vb at the first pump electrode 111 to a command voltage Vb (com).

The output terminal of an amplifier circuit 220 in the control circuit 202 is connected to one end of a current sensing resistor 250. The other end of the resistor 250 is connected to a second pump electrode 112 and a first sensor electrode 121. The resistor 250 acts to sense a pump cell current Ip. The voltage at the second pump electrode 112 and the first sensor electrode 121 is fed back to the inverting input terminal of the amplifier circuit 220. Accordingly, the amplifier circuit 220 equalizes the voltage at the second pump electrode 112 and the first sensor electrode 121 to a predetermined reference voltage Va.

An applied voltage command circuit 290 (a pump voltage command circuit 230) in the control circuit 202 stores information of the reference voltage Va. The applied voltage command circuit 290 (the pump voltage command circuit 230) is informed of the voltage Vd at the junction between the resistor 250 and the output terminal of the amplifier circuit 220. The applied voltage command circuit 290 (the pump voltage command circuit 230) calculates the pump cell current Ip from the voltages Va and Vd according to the following equation.

$$Ip=(Va-Vd)/R1$$

where R1 denotes the resistance of the resistor 250. It is possible to omit the analog-to-digital converter A/D2 (see FIG. 10) from the applied voltage command circuit 290 in the control circuit 202.

Since the resistor 250 is connected in common to the second pump electrode 112 and the first sensor electrode 121, a sensor cell current Is is superimposed on the pump cell current Ip which flows through the resistor 250. The magnitude of the sensor cell current Is is negligible with respect to that of the pump cell current Ip. Therefore, the sensor cell current Is is prevented from adversely affecting the voltage Vd at the junction between the resistor 250 and the output terminal of the amplifier circuit 220.

Fourth Embodiment

Figure 16:
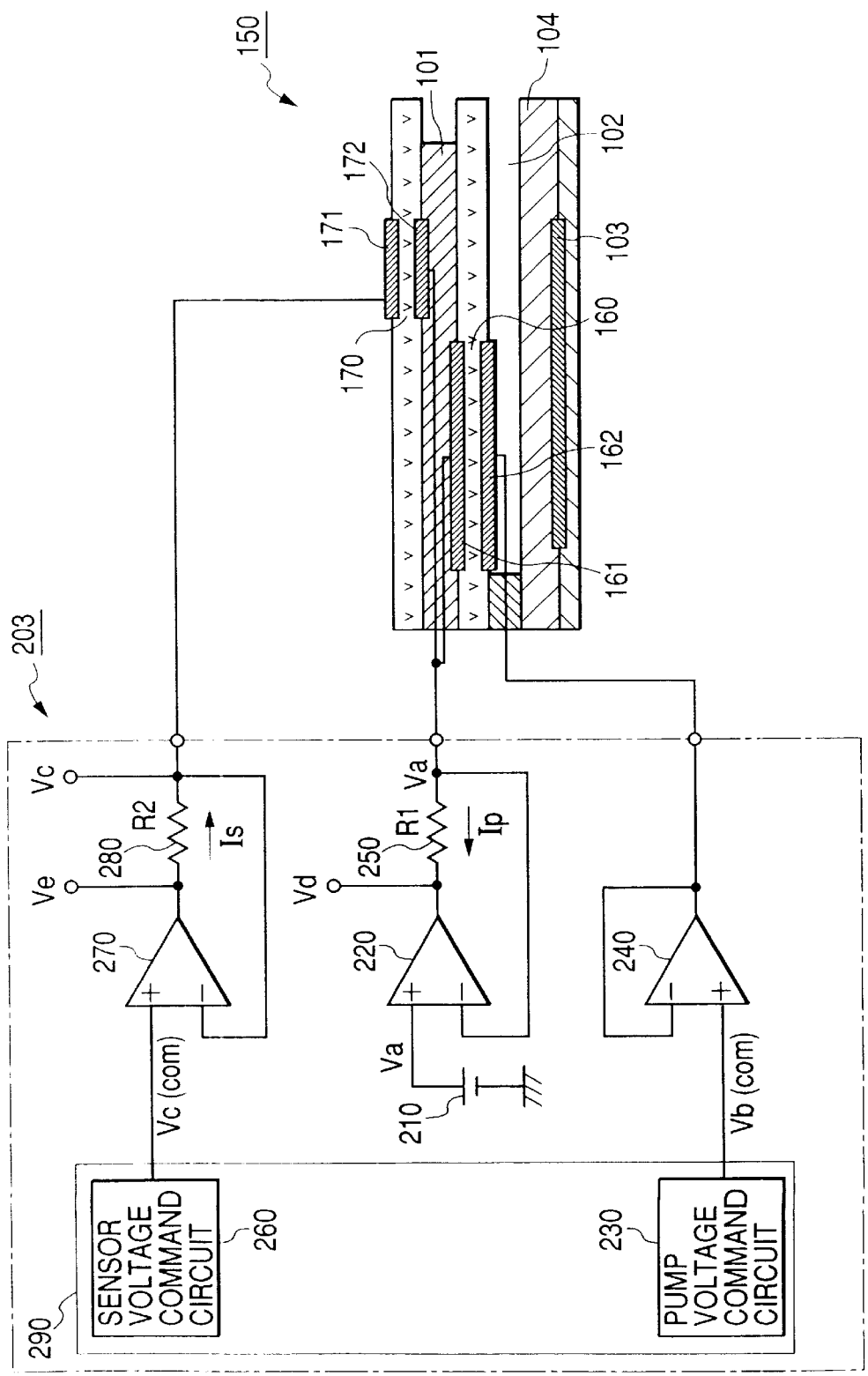
FIG. 16 is a diagram of a gas concentration sensing apparatus according to a fourth embodiment of this invention.

FIG. 16 shows a fourth embodiment of this invention which is similar to the second embodiment thereof except for design changes mentioned later. The embodiment of FIG. 16 includes a control circuit 203 which replaces the control circuit 201 in FIG. 14.

As shown in FIG. 16, the output terminal of an amplifier circuit 240 in the control circuit 203 is directly connected to a second pump electrode 162. Also, the output terminal of the amplifier circuit 240 is connected to the inverting input terminal thereof. The amplifier circuit 240 equalizes the voltage at the second pump electrode 162 to a command voltage Vb (com).

The output terminal of an amplifier circuit 220 in the control circuit 203 is connected to one end of a current sensing resistor 250. The other end of the resistor 250 is connected to a first pump electrode 161 and a second sensor electrode 172. The resistor 250 acts to sense a pump cell current Ip. The voltage at the first pump electrode 161 and the second sensor electrode 172 is fed back to the inverting input terminal of the amplifier circuit 220. Accordingly, the amplifier circuit 220 equalizes the voltage at the first pump electrode 161 and the second sensor electrode 172 to a predetermined reference voltage Va.

An applied voltage command circuit 290 (a pump voltage command circuit 230) in the control circuit 203 stores information of the reference voltage Va. The applied voltage command circuit 290 (the pump voltage command circuit 230) is informed of the voltage Vd at the junction between the resistor 250 and the output terminal of the amplifier circuit 220. The applied voltage command circuit 290 (the pump voltage command circuit 230) calculates the pump cell current Ip from the voltages Va and Vd according to the following equation.

$$Ip=(Va-Vd)/R1$$

where R1 denotes the resistance of the resistor 250. It is possible to omit the analog-to-digital converter A/D2 (see FIG. 10) from the applied voltage command circuit 290 in the control circuit 202.

Fifth Embodiment

Figure 17:
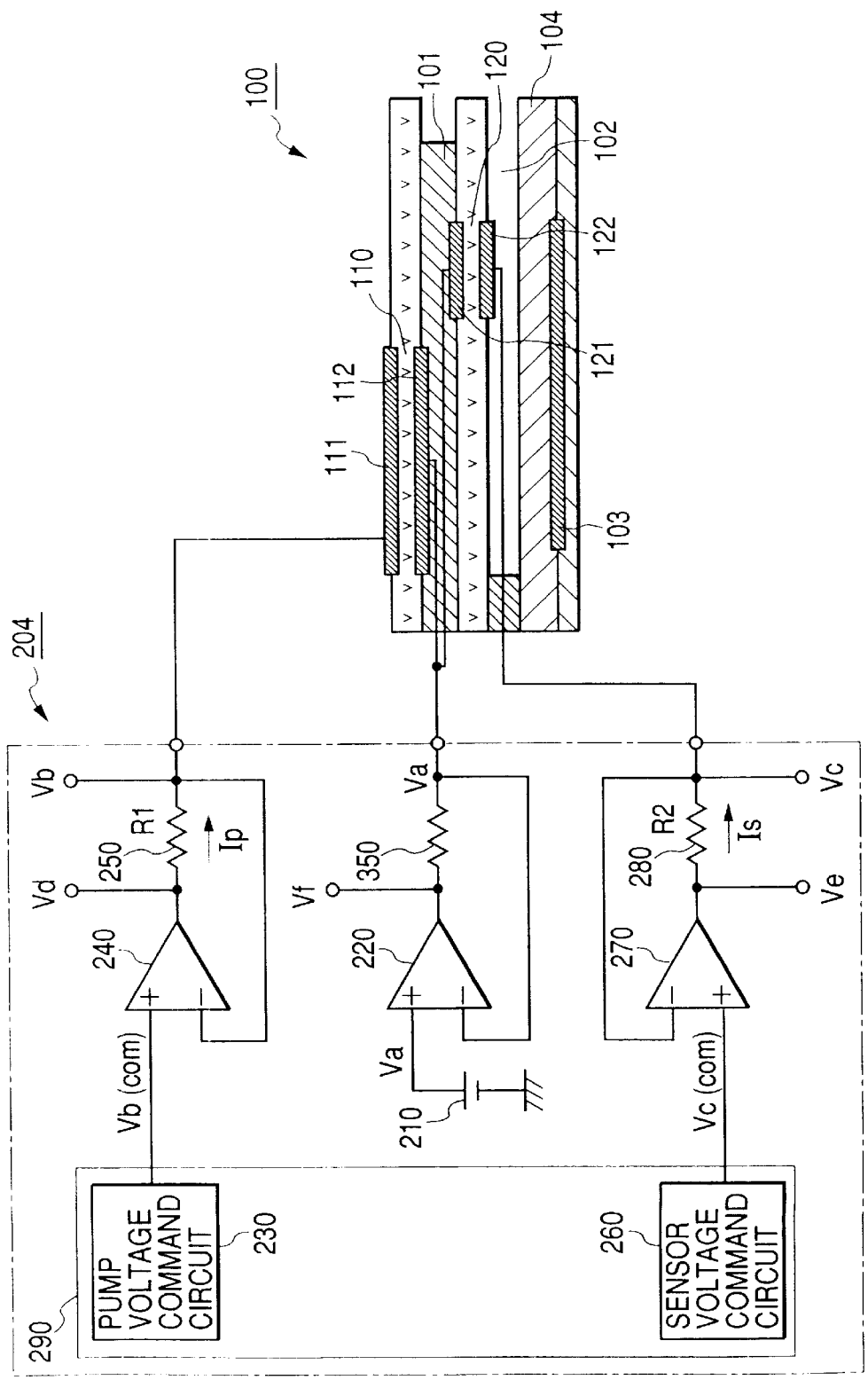
FIG. 17 is a diagram of a gas concentration sensing apparatus according to a fifth embodiment of this invention.

FIG. 17 shows a fifth embodiment of this invention which is similar to the first embodiment thereof except for design changes mentioned later. The embodiment of FIG. 17 includes a control circuit 204 which replaces the control circuit 200 in FIG. 9. The control circuit 204 is connected to a gas concentration sensor 100. The gas concentration sensor 100 has a pump cell 110 and a sensor cell 120. The control circuit 204 is designed to detect both the impedance of the pump cell 110 and the impedance of the sensor cell 120.

Figure 18:
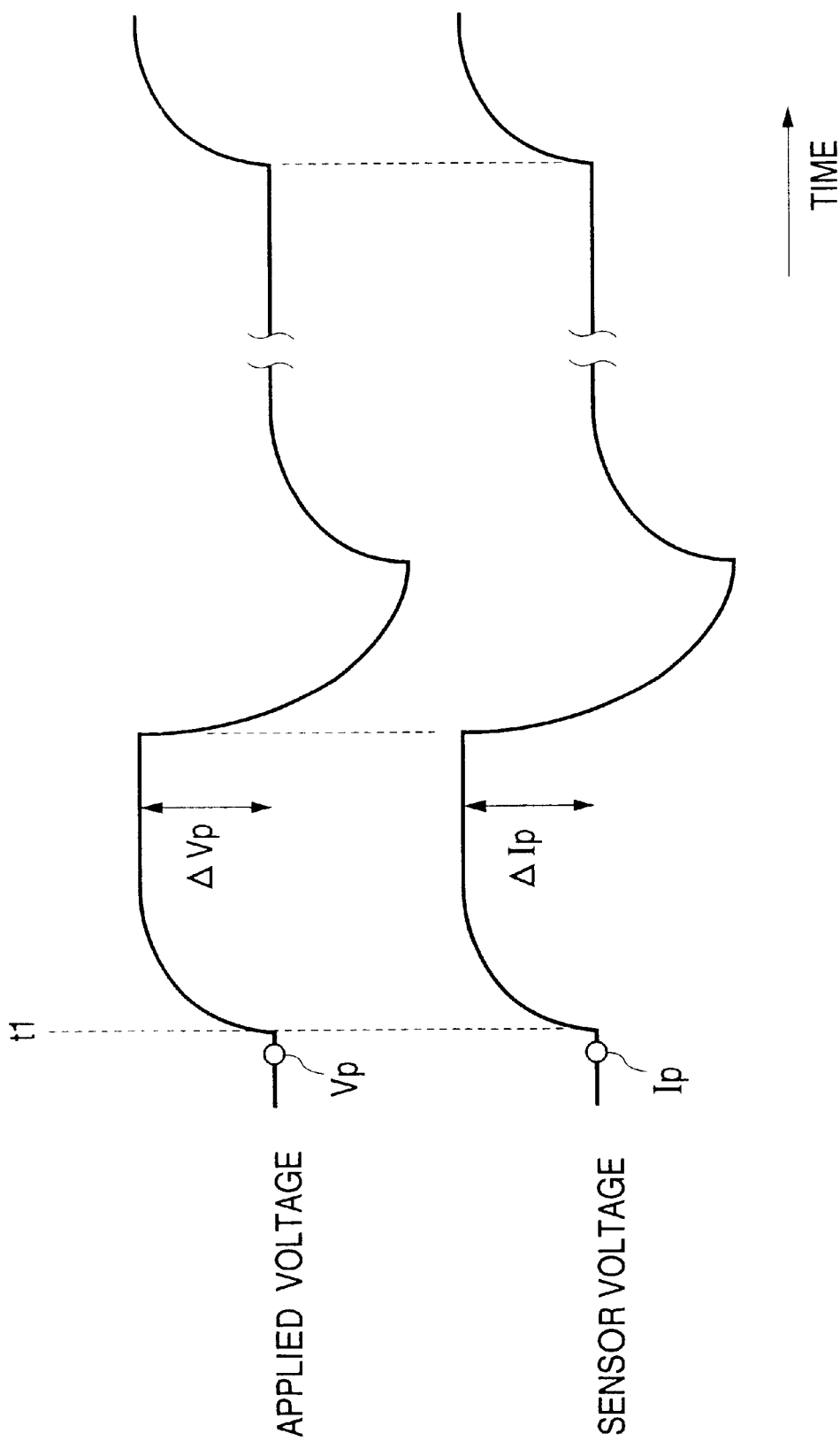
FIG. 18 is a time-domain diagram of a pump cell applied voltage and a pump cell current.

With reference to FIG. 18, before a moment t1, a voltage Vp is applied to the pump cell 110. The pump cell applied voltage Vp is determined on the basis of a detected pump current Ip according to the line LX1 in FIG. 5. At the moment t1, the detection of the impedance of the pump cell 110 is started. Specifically, at the moment t1, an ac voltage having a frequency of several kHz to several tens of kHz is superimposed on the pump cell applied voltage Vp. Measurement is made as to a voltage change quantity ΔVp and a current change quantity ΔIp responsive to the superimposed ac voltage. The voltage change quantity ΔVp means a quantity of a change in the voltage Vp. The current change quantity ΔIp means a quantity of a change in the current Ip. The impedance Rp of the pump cell 110 is calculated from the voltage change quantity ΔVp and the current change quantity ΔIp according to an equation as "Rp=ΔVp/ΔIp". Similarly, the impedance Rs of the sensor cell 120 is calculated.

Figure 19:
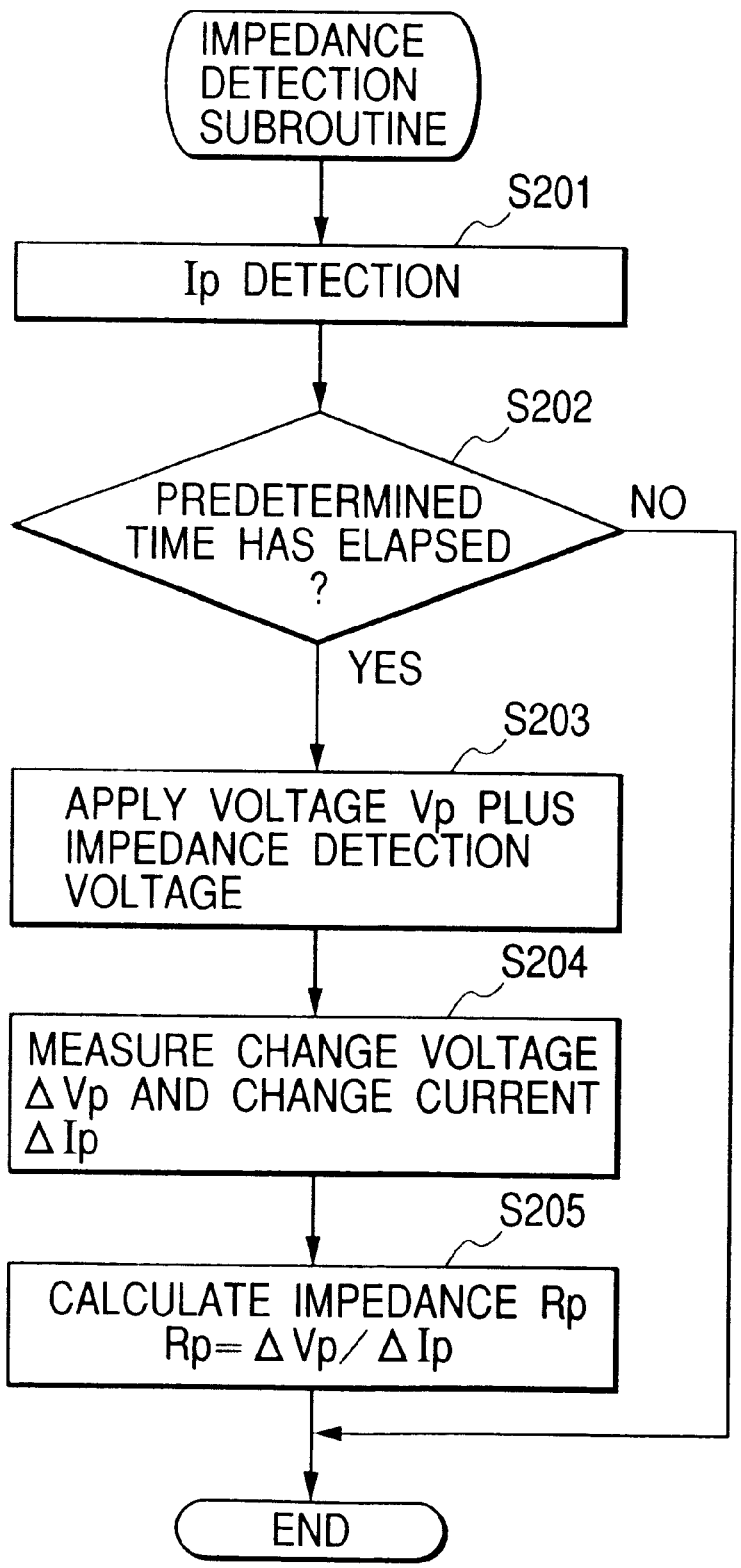
FIG. 19 is a flowchart of a subroutine of a control program for an applied voltage command circuit in FIG. 17.

FIG. 19 is a flowchart of a subroutine of a control program for an applied voltage command circuit 290 in the control circuit 204. The subroutine in FIG. 19 relates to the detection of the impedance Rp of the pump cell 110. The subroutine in FIG. 19 is periodically iterated by, for example, a timer-based interruption process during the execution of a main routine (not shown) of the control program.

As shown in FIG. 19, a first step S201 of the subroutine calculates a pump cell current Ip from the present values of voltages Vd and Vb, and the resistance R1 of a current sensing resistor 250 according to an equation as "Ip=(Vd−Vb)/R1".

A step S202 following the step S201 determines whether or not a predetermined time (for example, 128 ms) has elapsed since the moment of the last impedance detection. When the predetermined time has elapsed, the program advances from the step S202 to a step S203. Otherwise, the program exits from the step S202 and then the current execution cycle of the subroutine ends.

The step S203 superimposes a given ac voltage on the pump cell applied voltage Vp. A step S204 following the step S203 calculates a voltage change quantity ΔVp and a current change quantity ΔIp, which are responsive to the superimposed ac voltage, from the value of a predetermined reference voltage Va and the values of the voltages Vd and Vb derived through analog-to-digital converters in the applied voltage command circuit 290.

A step S205 subsequent to the step S204 calculates the impedance Rp of the pump cell 110 from the voltage change quantity ΔVp and the current change quantity ΔIp according to the equation "Rp=ΔVp/ΔIp". After the step S205, the current execution cycle of the subroutine ends.

Similarly, the impedance Rs of the sensor cell 120 is calculated. Specifically, a sensor cell current Is is calculated from the present values of voltages Ve and Vc, and the resistance R2 of a current sensing resistor 280 according to an equation as "Is=(Ve−Vc)/R2". Each time a predetermined time (for example, 128 ms) has elapsed, a given ac voltage is superimposed on the sensor cell applied voltage Vs. Measurement is made as to a voltage change quantity ΔVs and a current change quantity ΔIs, which are responsive to the superimposed ac voltage, from the value of the reference voltage Va and the values of the voltages Ve and Vc derived through analog-to-digital converters in the applied voltage command circuit 290. The voltage change quantity ΔVs means a quantity of a change in the voltage Vs. The current change quantity ΔIs means a quantity of a change in the current Is. The impedance Rs of the sensor cell 120 is calculated from the voltage change quantity ΔVs and the current change quantity ΔIs according to an equation as "Rs=ΔVs/ΔIs".

It is assumed that the impedance Rp of the pump cell 110 is equal to 45 Ω and the impedance Rs of the sensor cell 120 is equal to 200 Ω, and the amplitude ΔV of the given ac voltage used during the impedance detection is equal to 0.2 V. Furthermore, it is assumed that the analog-to-voltage converters in the applied voltage command circuit 290 can operate on input voltages each in the range of 0 to 5 V. In view of the input voltage range for the analog-to-voltage converters, the ac voltage amplitude ΔV is set to a lower limit value of a range in which an adequate accuracy of the impedance detection is available.

In this case, an additional current ΔIp flowing through the pump cell 110 is given as follows.

$$\Delta Ip = 0.2\ (V)/45(\Omega) = 4.44\ (mA)$$

In addition, an additional current ΔIs flowing through the pump cell 120 is given as follows.

$$\Delta Is = 0.2\ (V)/200(\Omega) = 1\ (mA)$$

The additional current ΔIp is superimposed on the pump cell current Ip. When the pump cell current Ip varies in the range of 0 to 4 mA in response to the oxygen ($O_2$) concentration in the exhaust gas, the sum of the pump cell current Ip and the additional current ΔIp can vary in the range of 0 to 8.44 mA. The current sensing resistor 250 is designed to convert the current range of 0 to 8.44 mA into the voltage range of 0 to 5 V which agrees with the input voltage range for the related analog-to-voltage converter. Since the range of 0 to 8.44 mA is wider than the range of 0 to 4 mA, the detection accuracy drops accordingly. Specifically, the detection accuracy drops by about 47.4% (=4 mA/8.44 mA) in comparison with the designing where only the pump cell current Ip is detected.

The additional current ΔIs is superimposed on the sensor cell current Is. When the sensor cell current Is varies in the range of −800 μA to 10 μA in response to the NOx concentration in the exhaust gas and the air-to-fuel ratio of an air-fuel mixture causing the exhaust gas, the sum of the sensor cell current Is and the additional current ΔIs can vary in the range of −800 μA to 1010 μA. The current sensing resistor 280 is designed to convert the current range of −800 μA to 1010 μA into the voltage range of 0 to 5 V which agrees with the input voltage range for the related analog-to-voltage converter. Since the range of −800 μA to 1010 μA is wider than the range of −800 μA to 10 μA, the detection accuracy drops accordingly. Specifically, the detection accuracy drops by about 44.7% (=810 μA/1810 μA) in comparison with the designing where only the sensor cell current Is is detected.

The maximum level of the pump cell applied voltage is set to 1.0 V (when the pump cell current Ip is equal to 4 mA). The sensor cell applied voltage is set in the range of −0.5 V to 1.0 V. The sensor cell applied voltage is equal to −0.5 V when the sensor cell current Is is equal to −800 μA. The sensor cell applied voltage is equal to 1.0 V when the sensor cell current Is is equal to +10 μA. During the detection of the impedance of the pump cell 110, an ac voltage of 0.2 V is superimposed on the pump cell applied voltage. During the detection of the impedance of the sensor cell 120, an ac voltage of 0.2 V is superimposed on the sensor cell applied voltage. As previously mentioned, the input voltage range for the analog-to-digital converters extends between 0 and 5 V. Amplifier circuits 220, 240, and 270 in the control circuit 204 are powered by a battery voltage, that is, 12 V. The voltages Vb, Vd, Vc, and Ve inputted into the analog-to-digital converters vary in the range of 0.5 V to 5 V provided that the output voltages of the amplifier circuits 220, 240, and 270 vary between 0.5 V and 10 V.

To satisfy the above-mentioned conditions of the applied voltages and the above-mentioned conditions of the input voltage range for the analog-to-digital converters, it is preferable to set parameters as follows. The optimal value of the reference voltage Va, the resistance R1 of the current sensing resistor 250, and the resistance R2 of the current sensing resistor 280 in the absence of the impedance detection are set to 3.0 V, 250 Ω, and 2.5 kΩ, respectively. The optimal value of the reference voltage Va, the resistance R1 of the current sensing resistor 250, and the resistance R2 of the current sensing resistor 280 during the impedance detection are set to 2.2 V, 189 Ω, and 1.5 kΩ, respectively. Since the preferable resistance R1 of the current sensing resistor 250 is equal to 250 Ω in the absence of the impedance detection while the preferable resistance R1 is equal to 189 Ω during the impedance detection, it is understood that the accuracy of the detection of the pump cell current Ip related to the oxygen ($O_2$) concentration in the exhaust gas drops by a factor of 0.756 (189 Ω/250 Ω) during the impedance detection. Since the preferable resistance R2 of the current sensing resistor 280 is equal to 2.5 kΩ in the absence of the impedance detection while the preferable resistance R2 is equal to 1.5 kΩ during the impedance detection, it is understood that the accuracy of the detection of the sensor cell current Is drops by a factor of 0.6 (1.5 kΩ/2.5 kΩ) during the impedance detection.

The control circuit 204 is designed to suppress the drop in the accuracy of the detection of the oxygen ($O_2$) concentration and the NOx concentration in the exhaust gas. As shown in FIG. 17, the output terminal of the amplifier circuit 220 in the control circuit 204 is connected to one end of an impedance sensing resistor 350. The other end of the resistor 350 is connected to a second pump electrode 112 and a first sensor electrode 121. The resistor 350 is used to sense the impedances of the pump cell 110 and the sensor cell 120. The voltage at the second pump electrode 112 and the first sensor electrode 121 is fed back to the inverting input terminal of the amplifier circuit 220. Accordingly, the amplifier circuit 220 equalizes the voltage at the second pump electrode 112 and the first sensor electrode 121 to the reference voltage Va.

The current sensing resistor 250 is used in detecting the pump cell current Ip depending on the oxygen ($O_2$) concentration in the exhaust gas. The current sensing resistor 250 is not used in detecting an ac current depending on the impedance of the pump cell 110. The current sensing resistor 280 is used in detecting the sensor cell current Is which depends on the NOx concentration in the exhaust gas and the air-to-fuel ratio of an air-fuel mixture causing the exhaust gas. The current sensing resistor 280 is not used in detecting an ac current depending on the impedance of the sensor cell 120. An ac current caused by the superimposed ac voltage is detected from the voltage difference (Vf–Va), that is, the voltage across the impedance sensing resistor 350 where Vf denotes the voltage at the junction between the resistor 350 and the output terminal of the amplifier circuit 220.

The actual value of the reference voltage Va, the actual resistance R1 of the current sensing resistor 250, and the actual resistance R2 of the current sensing resistor 280 are set to 3.0 V, 250 Ω, and 2.5 kΩ, respectively. The resistance of the impedance sensing resistor 350 is set to 200 Ω. Since the current sensing resistors 250 and 280 are not used for the detection of ac currents during the impedance detection, it is unnecessary to reduce their resistances R1 and R2 from 250 Ω and 2.5 kΩ respectively. Accordingly, it is possible to prevent the accuracy of the detection of the gas concentrations from being dropped by the impedance detection.

During the detection of the impedance of the pump cell 110, when the pump cell applied voltage is equal to 1 V and the impedance-detecting ac voltage is equal to 0.2 V, the pump cell current Ip is maximized to 4 mA. In this case, provided that the sensor cell current Is is equal to 0 mA, the voltages Vb, Vd, and Vf are maximized as follows.

$Vb$=4.2 V (=3 V+1 V+0.2 V)

$Vd$=6.31 V (=(4 mA +4.44 mA)·250 Ω+4.2 V)

$Vf$=1.312 V (=3 V–(4 mA +4.44 mA)·200 Ω)

It should be noted that the reference voltage Va is equal to 3.0 V. Although the voltage Vd exceeds 5 V, the voltage Vd remains not read during the impedance detection. Therefore, the voltage Vd higher than 5 V causes no problem during the impedance detection. A 5-V clamping circuit may be provided in a stage preceding the analog-to-digital converter which handles the voltage Vd.

During the detection of the impedance of the sensor cell 120, when the sensor cell applied voltage is equal to 1 V and the impedance-detecting ac voltage is equal to 0.2 V, the pump cell current Is is maximized to 10 µA. In this case, provided that the pump cell current Ip is equal to 0 mA, the voltages Vc, Ve, and Vf are maximized as follows.

$Vc$=4.2 V (=3 V+1 V+0.2 V)

$Ve$=6.73 V (=(10 µA+1 mA)·2.5 kΩ+4.2 V)

$Vf$=2.798 V (=3 V–(10 µA+1 mA)·200 Ω)

It should be noted that the reference voltage Va is equal to 3.0 V. Although the voltage Ve exceeds 5 V, the voltage Ve remains not read during the impedance detection. Therefore, the voltage Ve higher than 5 V causes no problem during the impedance detection. A 5-V clamping circuit may be provided in a stage preceding the analog-to-digital converter which handles the voltage Ve.

Sixth Embodiment

Figure 20:
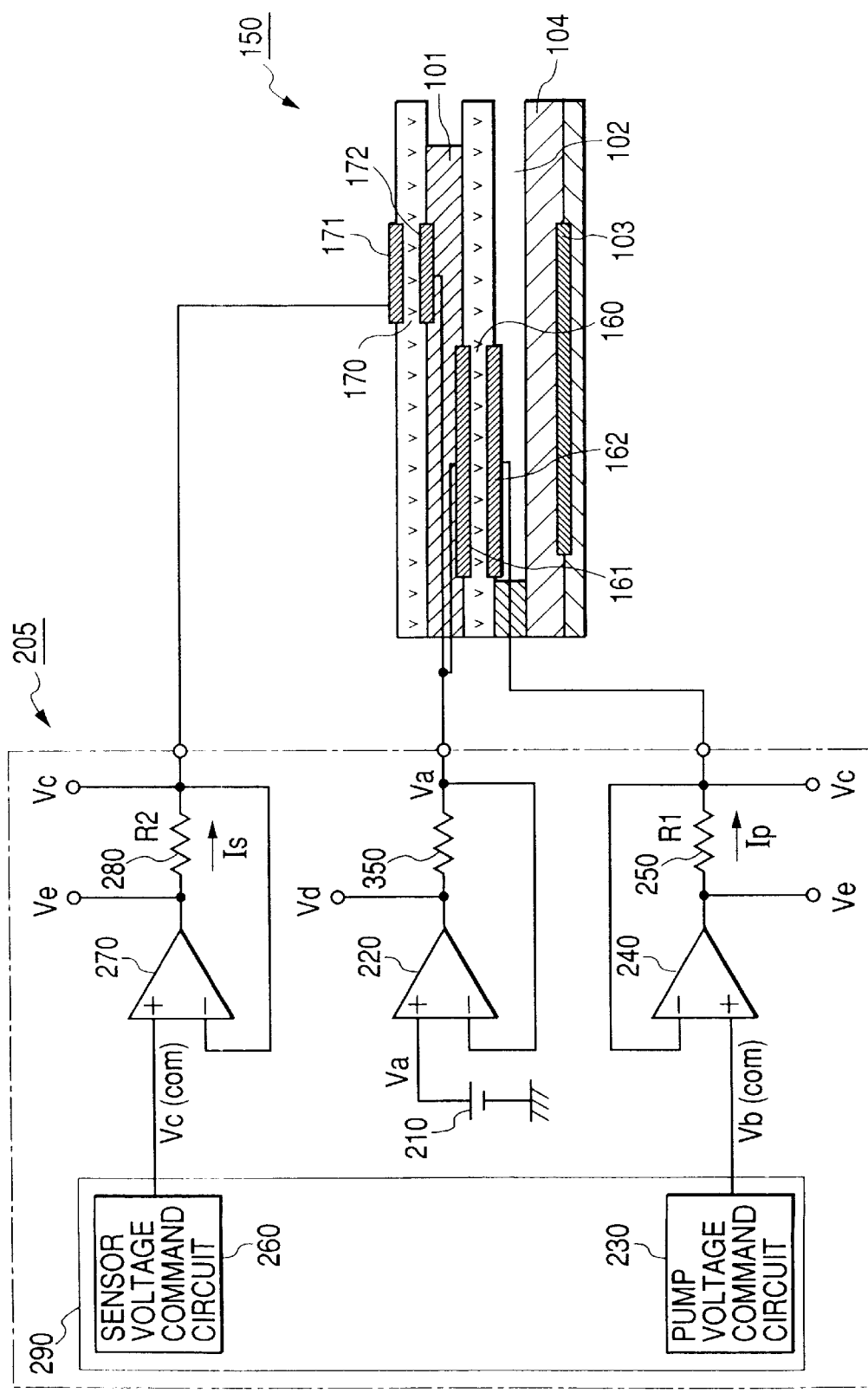
FIG. 20 is a diagram of a gas concentration sensing apparatus according to a sixth embodiment of this invention.

FIG. 20 shows a sixth embodiment of this invention which is similar to the fifth embodiment thereof except for design changes mentioned later. The embodiment of FIG. 20 includes a gas concentration sensor 150 which replaces the gas concentration sensor 100 in FIG. 17. The gas concentration sensor 150 is similar to that in FIG. 12. The embodiment of FIG. 20 includes a control circuit 205 which replaces the control circuit 204 in FIG. 17.

As shown in FIG. 20, the output terminal of an amplifier circuit 220 in the control circuit 205 is connected to one end of an impedance sensing resistor 350. The other end of the resistor 350 is connected to a first pump electrode 161 and a second sensor electrode 172. The resistor 350 is used to sense the impedances of a pump cell 160 and a sensor cell 170 in the gas concentration sensor 150. The voltage at the first pump electrode 161 and the second sensor electrode 172 is fed back to the inverting input terminal of the amplifier circuit 220. Accordingly, the amplifier circuit 220 equalizes the voltage at the first pump electrode 161 and the second sensor electrode 172 to a predetermined reference voltage Va. The output terminal of an amplifier circuit 240 in the control circuit 205 is connected via a current sensing resistor 250 to a second pump electrode 162. The output terminal of an amplifier circuit 270 in the control circuit 205 is connected via a current sensing resistor 280 to a first sensor electrode 171.

The impedance sensing resistor 350 is used to detect an ac current change during the impedance detection. The current sensing resistor 250 is used in detecting a pump cell current Ip which depends on the oxygen ($O_2$) concentration in an exhaust gas and the air-to-fuel ratio of an air-fuel mixture causing the exhaust gas. The current sensing resistor 250 is not used in detecting an ac current depending on the impedance of the pump cell 110. The current sensing resistor 280 is used in detecting a sensor cell current Is which depends on the NOx concentration in the exhaust gas. The current sensing resistor 280 is not used in detecting an ac current depending on the impedance of the sensor cell 120. An ac current caused by a superimposed ac voltage is detected from the voltage difference (Vd–Va), that is, the voltage across the impedance sensing resistor 350 where Vd denotes the voltage at the junction between the resistor 350 and the output terminal of the amplifier circuit 220.

Seventh Embodiment

Figure 21:
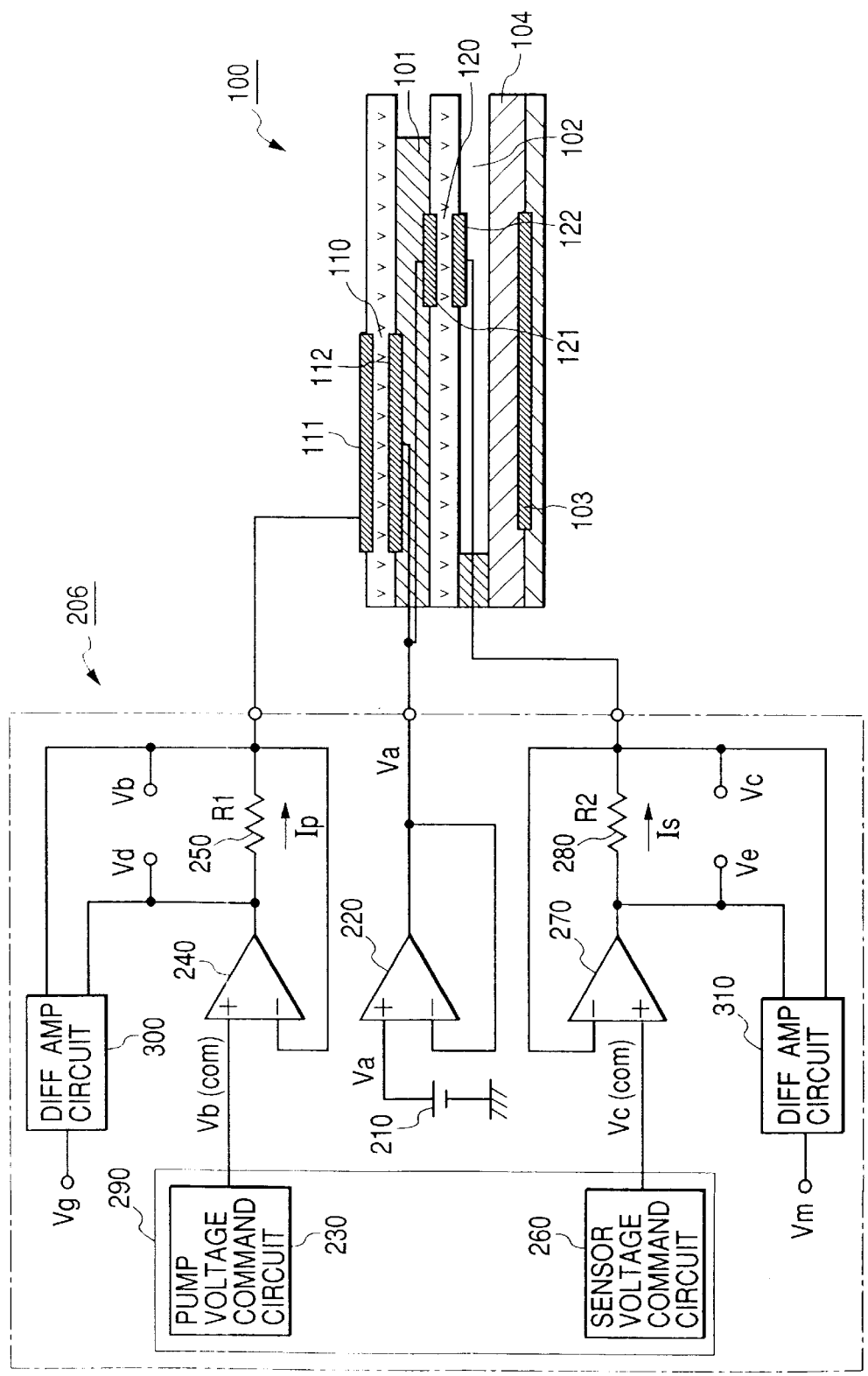
FIG. 21 is a diagram of a gas concentration sensing apparatus according to a seventh embodiment of this invention.

FIG. 21 shows a seventh embodiment of this invention which is similar to the fifth embodiment thereof except for design changes mentioned later. The embodiment of FIG. 21 includes a control circuit 206 which replaces the control circuit 204 in FIG. 17.

As shown in FIG. 21, the output terminal of an amplifier circuit 220 in the control circuit 206 is directly connected to a second pump electrode 112 and a first sensor electrode 121. The voltage at the second pump electrode 112 and the first sensor electrode 121 are fed back to the inverting input terminal of the amplifier circuit 220. Thus, the amplifier circuit 220 equalizes the voltage at the second pump electrode 112 and the first sensor electrode 121 to a predetermined reference voltage Va.

The control circuit 206 includes a differential amplifier circuit 300 connected to the opposite ends of a current sensing resistor 250. The differential amplifier circuit 300 receives voltages Vb and Vd which appear at the opposite ends of the resistor 250 respectively. The differential amplifier circuit 300 outputs a voltage Vg proportional to the voltage difference (Vd–Vb). The output voltage Vg of the differential amplifier circuit 300 is fed to an applied voltage command circuit 290 in the control circuit 206. The applied voltage command circuit 290 includes an analog-to-digital converter which handles the output voltage Vg of the differential amplifier circuit 300. The applied voltage command circuit 290 detects a pump cell current Ip, which depends on the oxygen ($O_2$) concentration in an exhaust gas, from the output voltage Vg of the differential amplifier circuit 300. Also, the applied voltage command circuit 290 detects a sensing current, which relates to the impedance of a pump cell 110, from the output voltage Vg of the differential amplifier circuit 300.

The control circuit 206 includes a differential amplifier circuit 310 connected to the opposite ends of a current sensing resistor 280. The differential amplifier circuit 310 receives voltages Vc and Ve which appear at the opposite ends of the resistor 280 respectively. The differential amplifier circuit 310 outputs a voltage Vm proportional to the voltage difference (Ve−Vc). The output voltage Vm of the differential amplifier circuit 310 is fed to the applied voltage command circuit 290. The applied voltage command circuit 290 includes an analog-to-digital converter which handles the output voltage Vm of the differential amplifier circuit 310. The applied voltage command circuit 290 detects a sensor cell current Is, which depends on the NOx concentration in the exhaust gas and the air-to-fuel ratio of an air-fuel mixture causing the exhaust gas, from the output voltage Vm of the differential amplifier circuit 310. Also, the applied voltage command circuit 290 detects a sensing current, which relates to the impedance of a sensor cell 120, from the output voltage Vm of the differential amplifier circuit 310.

The value of the reference voltage Va, the resistance R1 of the current sensing resistor 250, and the resistance R2 of the current sensing resistor 280 are preferably set to 3.0 V, 250 $\Omega$, and 2.5 k$\Omega$, respectively. In this case, preferable conditions of applied voltages, preferable conditions of detected currents, and preferable conditions of input voltages into analog-to-digital converters are satisfied. It is unnecessary to reduce the resistance R1 of the current sensing resistor 250 and the resistance R2 of the current sensing resistor 280 due to the detection of ac currents during the impedance detection. Accordingly, it is possible to prevent the accuracy of the detection of the gas concentrations from being dropped by the impedance detection.

During the detection of the impedance of the pump cell 110, when the pump cell applied voltage is equal to 1 V and the impedance-detecting ac voltage is equal to 0.2 V, the pump cell current Ip is maximized to 4 mA. In this case, provided that the sensor cell current Is is equal to 0 mA, the voltages Vb and Vd are maximized as follows.

$$Vb = 4.2 \text{ V} (= 3 \text{ V} + 1 \text{ V} + 0.2 \text{ V})$$

$$Vd = 6.31 \text{ V} (= (4 \text{ mA} + 4.44 \text{ mA}) \cdot 250 \, \Omega + 4.2 \text{ V})$$

It should be noted that the reference voltage Va is equal to 3.0 V. The voltage Vd exceeds 5 V. The output voltage Vg of the differential amplifier circuit 300 is given as follows.

$$Vg = (Vd - Vb) \cdot \beta 1$$

where $\beta 1$ denotes the gain of the differential amplifier circuit 300. The gain $\beta 1$ of the differential amplifier circuit 300 is chosen to limit the voltage Vg to 5 V or less. Therefore, the voltage Vd higher than 5 V causes no problem during the impedance detection.

During the detection of the impedance of the sensor cell 120, when the sensor cell applied voltage is equal to 1 V and the impedance-detecting ac voltage is equal to 0.2 V, the pump cell current Is is maximized to 10 $\mu$A. In this case, provided that the pump cell current Ip is equal to 0 mA, the voltages Vc and Ve are maximized as follows.

$$Vc = 4.2 \text{ V} (= 3 \text{ V} + 1 \text{ V} + 0.2 \text{ V})$$

$$Ve = 6.73 \text{ V} (= (10 \, \mu\text{A} + 1 \text{ mA}) \cdot 2.5 \text{ k}\Omega + 4.2 \text{ V})$$

It should be noted that the reference voltage Va is equal to 3.0 V. The voltage Ve exceeds 5 V. The output voltage Vm of the differential amplifier circuit 310 is given as follows.

$$Vm = (Ve - Vc) \cdot \beta 2$$

where $\beta 2$ denotes the gain of the differential amplifier circuit 310. The gain $\beta 2$ of the differential amplifier circuit 310 is chosen to limit the voltage Vm to 5 V or less. Therefore, the voltage Ve higher than 5 V causes no problem during the impedance detection.

A suitable offset voltage may be provided to the differential amplifier circuit 310 to enable the differential amplifier circuit 310 to sense a negative sensor cell current Is. The applied voltage command circuit 290 may be directly informed of the voltages Ve and Vc which appear at the opposite ends of the current sensing resistor 280.

Eighth Embodiment

Figure 22:
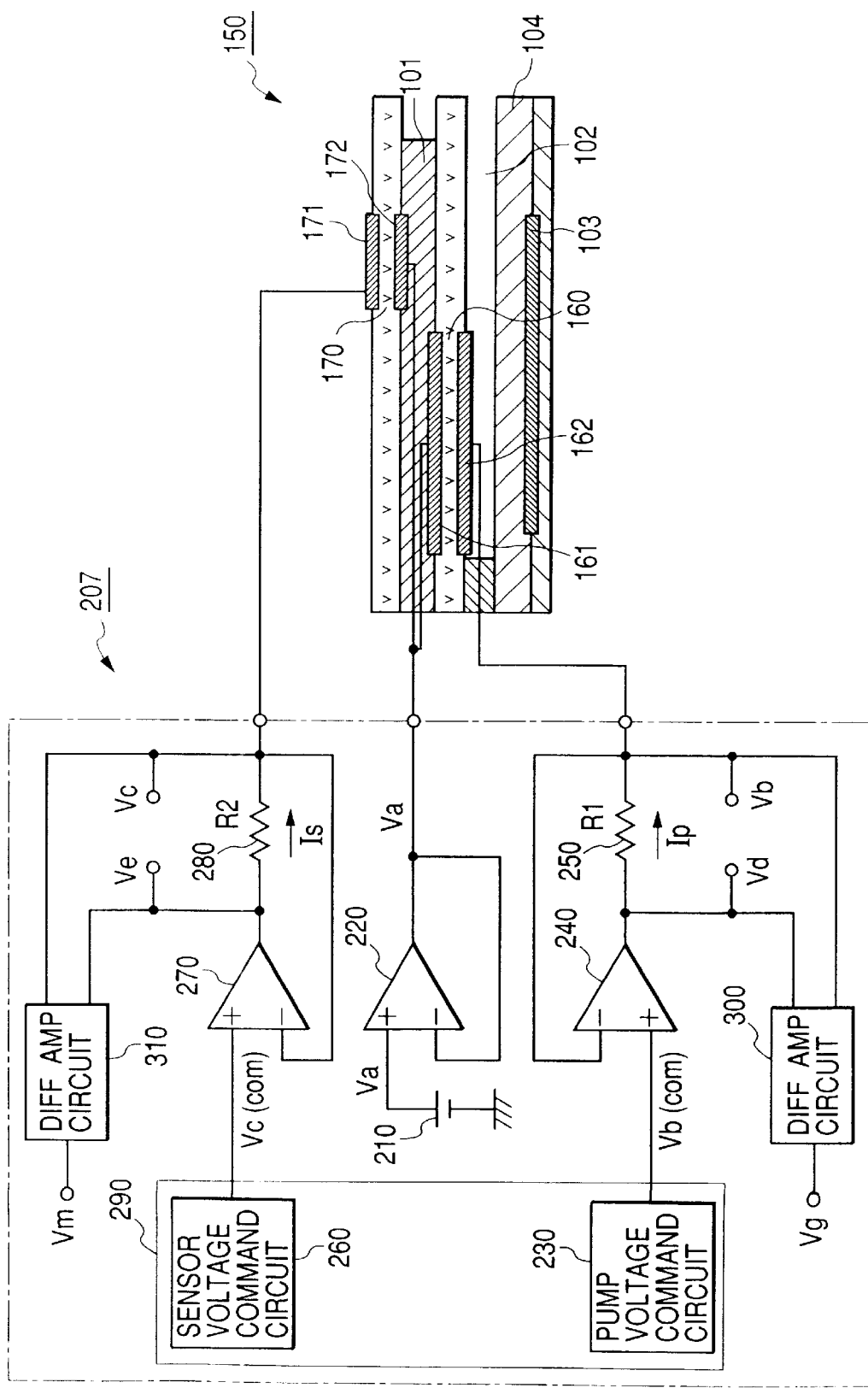
FIG. 22 is a diagram of a gas concentration sensing apparatus according to an eighth embodiment of this invention.

FIG. 22 shows an eighth embodiment of this invention which is similar to the seventh embodiment thereof except for design changes mentioned later. The embodiment of FIG. 22 includes a gas concentration sensor 150 which replaces the gas concentration sensor 100 in FIG. 21. The gas concentration sensor 150 is similar to that in FIG. 12. The embodiment of FIG. 22 includes a control circuit 207 which replaces the control circuit 206 in FIG. 21.

As shown in FIG. 22, the output terminal of an amplifier circuit 220 in the control circuit 207 is directly connected to a first pump electrode 161 and a second sensor electrode 172. The voltage at the first pump electrode 161 and the second sensor electrode 172 is fed back to the inverting input terminal of the amplifier circuit 220. Accordingly, the amplifier circuit 220 equalizes the voltage at the first pump electrode 161 and the second sensor electrode 172 to a predetermined reference voltage Va. The output terminal of an amplifier circuit 240 in the control circuit 207 is connected via a current sensing resistor 250 to a second pump electrode 162. The output terminal of an amplifier circuit 270 in the control circuit 207 is connected via a current sensing resistor 280 to a first sensor electrode 171.

The control circuit 207 includes a differential amplifier circuit 300 connected to the opposite ends of the current sensing resistor 250. The differential amplifier circuit 300 receives voltages Vb and Vd which appear at the opposite ends of the resistor 250 respectively. The differential amplifier circuit 300 outputs a voltage Vg proportional to the voltage difference (Vd−Vb). The output voltage Vg of the differential amplifier circuit 300 is fed to an applied voltage command circuit 290 in the control circuit 207. The applied voltage command circuit 290 detects a pump cell current Ip, which depends on the oxygen ($O_2$) concentration in an exhaust gas and the air-to-fuel ratio of an air-fuel mixture causing the exhaust gas, from the output voltage Vg of the differential amplifier circuit 300. Also, the applied voltage command circuit 290 detects a sensing current, which relates to the impedance of a pump cell 160, from the output voltage Vg of the differential amplifier circuit 300.

The control circuit 207 includes a differential amplifier circuit 310 connected to the opposite ends of the current sensing resistor 280. The differential amplifier circuit 310 receives voltages Vc and Ve which appear at the opposite ends of the resistor 280 respectively. The differential amplifier circuit 310 outputs a voltage Vm proportional to the voltage difference (Ve−Vc). The output voltage Vm of the differential amplifier circuit 310 is fed to the applied voltage command circuit 290. The applied voltage command circuit 290 detects a sensor cell current Is, which depends on the NOx concentration in the exhaust gas, from the output voltage Vm of the differential amplifier circuit 310. Also, the applied voltage command circuit 290 detects a sensing current, which relates to the impedance of a sensor cell 170, from the output voltage Vm of the differential amplifier circuit 310.

Ninth Embodiment

A ninth embodiment of this invention is similar to the first embodiment thereof except for design changes mentioned later. The ninth embodiment is designed to prevent a pump cell 110 from interfering with a sensor cell 120 (see FIG. 9) in sensing action.

When a gas concentration sensor 100 (see FIG. 9) is exposed to an exhaust gas originating from a rich air-fuel mixture, oxygen ($O_2$) is transferred from an atmosphere duct 102 to a porous diffusion layer 101 via the sensor cell 120. The oxygen ($O_2$) travels leftward (as viewed in FIG. 9) in the porous diffusion layer 101 while being diffused and controlled in rate. A portion of the oxygen ($O_2$) would move out of the porous diffusion layer 101 via the left-hand end surface thereof. The other portion of the oxygen ($O_2$) would be pumped from the porous diffusion layer 101 to an external space by the pump cell 110. In this case, the pump cell 110 would interfere with the sensor cell 120 in sensing action.

Figure 23:
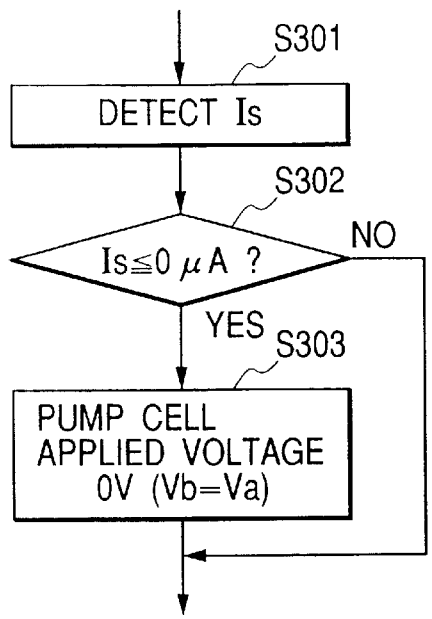
FIG. 23 is a flowchart of a portion of a subroutine of a control program for an applied voltage command circuit in a ninth embodiment of this invention.

FIG. 23 is a flowchart of a portion of a subroutine of a control program for an applied voltage command circuit 290 (see FIG. 9) in the ninth embodiment of this invention. As shown in FIG. 23, a step S301 detects a sensor cell current Is. A step S302 following the step S301 compares the detected sensor cell current Is with 0 µA to determine whether the detected sensor cell current Is is positive or negative. When the sensor cell current Is is equal to 0 µA or is negative, the program advances from the step S302 to a step S303. The step S303 sets a pump cell applied voltage to 0 V. Specifically, the step S303 sets a pump command voltage Vb(com) to a value of a predetermined reference voltage Va. As a result, a voltage Vb at a first pump electrode 111 is equalized to the reference voltage Va applied to a second pump electrode 112. In this case, a current hardly flows through the pump cell 110, and the pumping of oxygen ($O_2$) from the porous diffusion layer 101 to the external space via the pump cell 110 is forced to be suspended. After the step S303, the program advances to a next portion of the subroutine. When the step S302 determines that the sensor cell current Is is positive, the program jumps from the step S302 to the next portion of the subroutine.

When the gas concentration sensor 100 is exposed to an exhaust gas originating from a rich air-fuel mixture, the step S303 sets the pump cell applied voltage to 0 V so that the pumping of oxygen ($O_2$) from the porous diffusion layer 101 to the external space via the pump cell 110 is forced to be suspended. Accordingly, the pump cell 110 is prevented from interfering with the sensor cell 120 in sensing action.

The step S303 may set the pump cell applied voltage to a level near 0 V at which the pumping of oxygen ($O_2$) from the porous diffusion layer 101 to the external space via the pump cell 110 can be substantially suspended.

Tenth Embodiment

A tenth embodiment of this invention is similar to the second embodiment thereof except for design changes mentioned later. The tenth embodiment is designed to prevent a sensor cell 170 from interfering with a pump cell 160 (see FIGS. 12 and 14) in sensing action.

When a gas concentration sensor 150 (see FIGS. 12 and 14) is exposed to an exhaust gas originating from a rich air-fuel mixture, oxygen ($O_2$) is transferred from an atmosphere duct 102 to a porous diffusion layer 101 via the pump cell 160. The oxygen ($O_2$) travels in the porous diffusion layer 101 while being diffused and controlled in rate. A portion of the oxygen ($O_2$) would move out of the porous diffusion layer 101 via the left-hand end surface thereof. The other portion of the oxygen ($O_2$) would be transferred from the porous diffusion layer 101 to an external space by the sensor cell 170. In this case, the sensor cell 170 would interfere with the pump cell 160 in sensing action.

Figure 24:
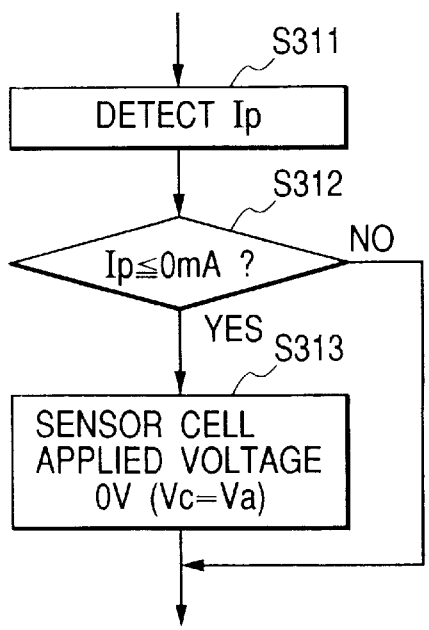
FIG. 24 is a flowchart of a portion of a subroutine of a control program for an applied voltage command circuit in a tenth embodiment of this invention.

FIG. 24 is a flowchart of a portion of a subroutine of a control program for an applied voltage command circuit 290 (see FIG. 14) in the tenth embodiment of this invention. As shown in FIG. 24, a step S311 detects a pump cell current Ip. A step S312 following the step S311 compares the detected pump cell current Ip with 0 mA to determine whether the detected pump cell current Ip is positive or negative. When the pump cell current Ip is equal to 0 mA or is negative, the program advances from the step S312 to a step S313. The step S313 sets a sensor cell applied voltage to 0 V. Specifically, the step S313 sets a sensor command voltage Vc(com) to a value of a predetermined reference voltage Va. As a result, a voltage Vc at a first sensor electrode 171 is equalized to the reference voltage Va applied to a second sensor electrode 172. In this case, a current hardly flows through the sensor cell 170, and the transfer of oxygen ($O_2$) from the porous diffusion layer 101 to the external space via the sensor cell 170 is forced to be suspended. After the step S313, the program advances to a next portion of the subroutine. When the step S312 determines that the pump cell current Ip is positive, the program jumps from the step S312 to the next portion of the subroutine.

When the gas concentration sensor 100 is exposed to an exhaust gas originating from a rich air-fuel mixture, the step S313 sets the sensor cell applied voltage to 0 V so that the transfer of oxygen ($O_2$) from the porous diffusion layer 101 to the external space via the sensor cell 170 is forced to be suspended. Accordingly, the sensor cell 170 is prevented from interfering with the pump cell 160 in sensing action.

The step S313 may set the sensor cell applied voltage to a level near 0 V at which the transfer of oxygen ($O_2$) from the porous diffusion layer 101 to the external space via the sensor cell 170 can be substantially suspended.

Eleventh Embodiment

Figure 25:
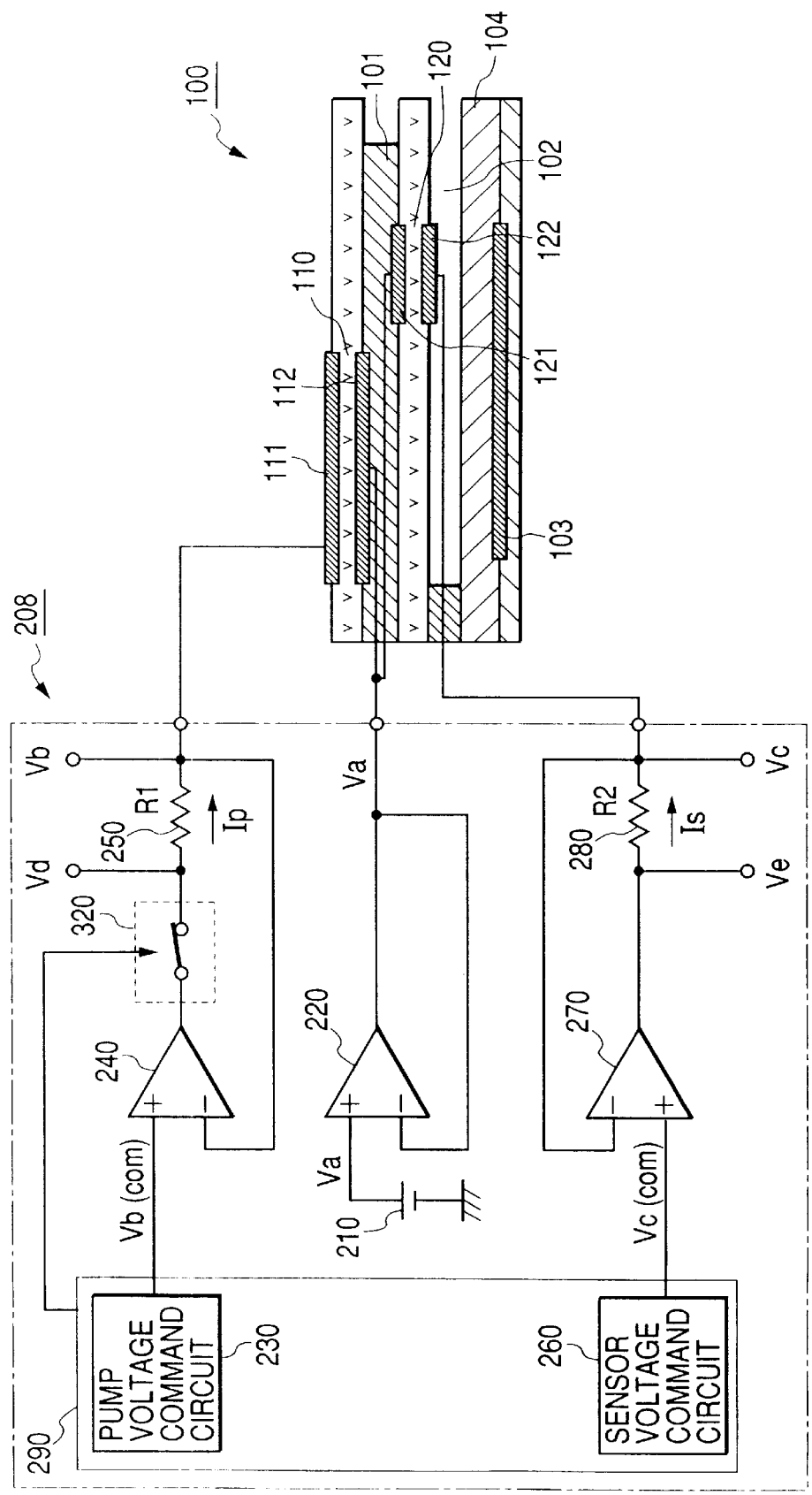
FIG. 25 is a diagram of a gas concentration sensing apparatus according to an eleventh embodiment of this invention.

FIG. 25 shows an eleventh embodiment of this invention which is similar to the ninth embodiment thereof except for design changes mentioned later. The embodiment of FIG. 25 includes a control circuit 208 which replaces the control circuit 200 in FIG. 9.

The control circuit 208 includes a switch circuit 320 interposed between a current sensing resistor 250 and the output terminal of an amplifier circuit 240. The switch circuit 320 is controlled by an applied voltage command circuit 290 in the control circuit 208. The switch circuit 320 is normally closed. When a negative current flows through a sensor cell 120, that is, when a gas concentration sensor 100 is exposed to an exhaust gas originating from a rich air-fuel mixture, the applied voltage command circuit 290 opens the switch circuit 320 to remove the voltage application from a pump cell 110. As a result, the pump cell 110 is prevented from interfering with the sensor cell 120 in sensing action.

Figure 26:
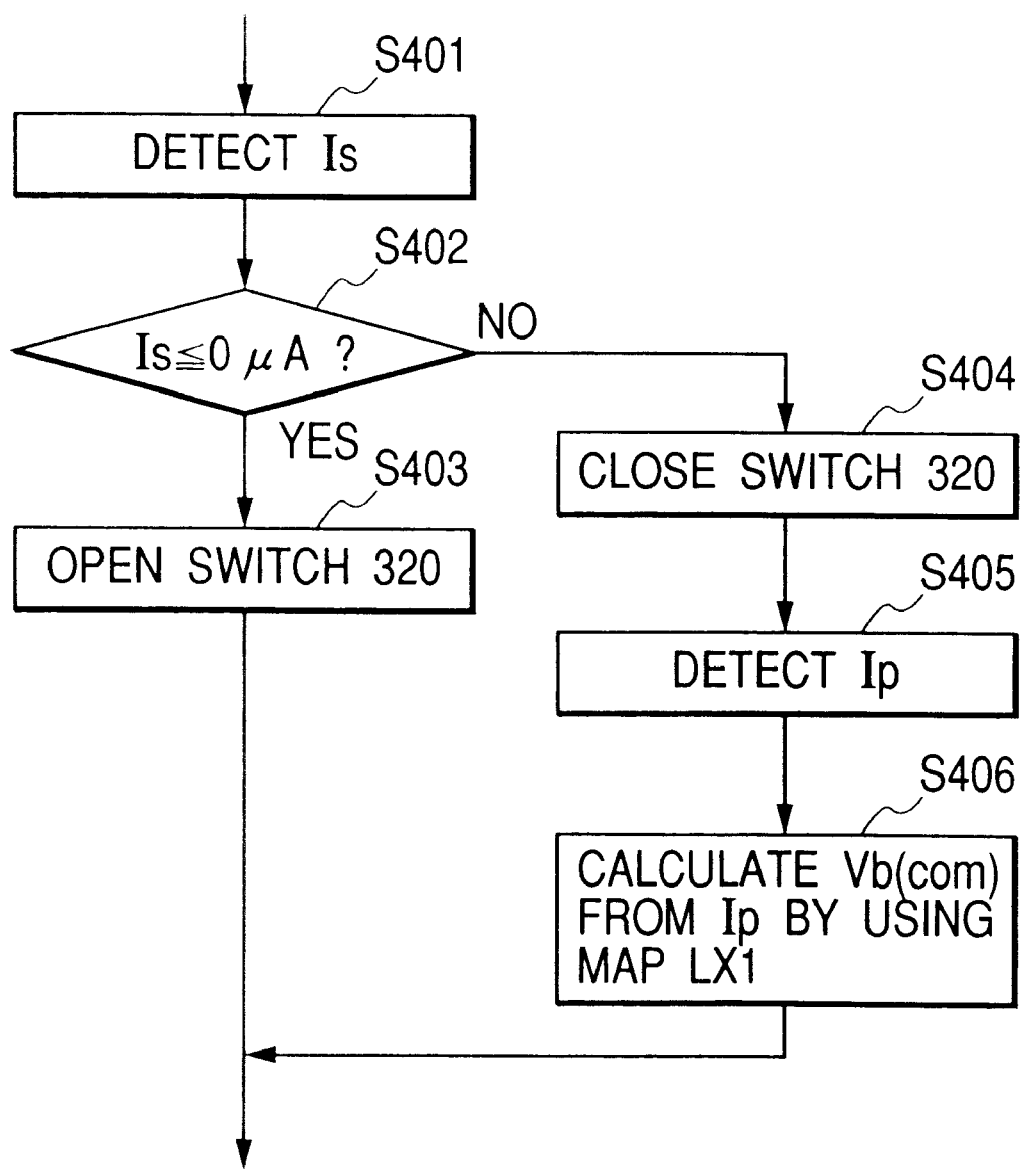
FIG. 26 is a flowchart of a portion of a subroutine of a control program for an applied voltage command circuit in FIG. 25.

FIG. 26 is a flowchart of a portion of a subroutine of a control program for the applied voltage command circuit 290 in the eleventh embodiment of this invention. As shown in FIG. 26, a step S401 calculates a sensor cell current Is according to an equation as "Is=(Ve−Vc)/R2". A step S402 following the step S401 compares the detected sensor cell current Is with 0 μA to determine whether the detected sensor cell current Is is positive or negative. When the sensor cell current Is is equal to 0 μA or is negative, the program advances from the step S402 to a step S403. The step S403 opens the switch circuit 320. As a result, the voltage application is removed from the pump cell 110. In this case, a current hardly flows through the pump cell 110, and the pumping of oxygen ($O_2$) from a porous diffusion layer 101 to an external space via the pump cell 110 is forced to be suspended. After the step S403, the program advances to a next portion of the subroutine.

When the step S402 determines that the sensor cell current Is is positive, the program advances from the step S402 to a step S404. The step 404 closes the switch circuit 320 so that an effective voltage can be applied to the pump cell 110. A step S405 following the step S404 calculates a pump cell current Ip according to an equation as "Ip=(Vd−Vb)/R1". A step S406 subsequent to the step S405 calculates a target pump command voltage Vb(com) from the pump cell current Ip by referring to the line LX1 in FIG. 5. After the step S406, the program advances to the next portion of the subroutine.

When the gas concentration sensor 100 is exposed to an exhaust gas originating from a rich air-fuel mixture, the step S403 opens the switch circuit 320 so that the pumping of oxygen ($O_2$) from the porous diffusion layer 101 to the external space via the pump cell 110 is forced to be suspended. Accordingly, the pump cell 110 is prevented from interfering with the sensor cell 120 in sensing action.

Twelfth Embodiment

Figure 27:
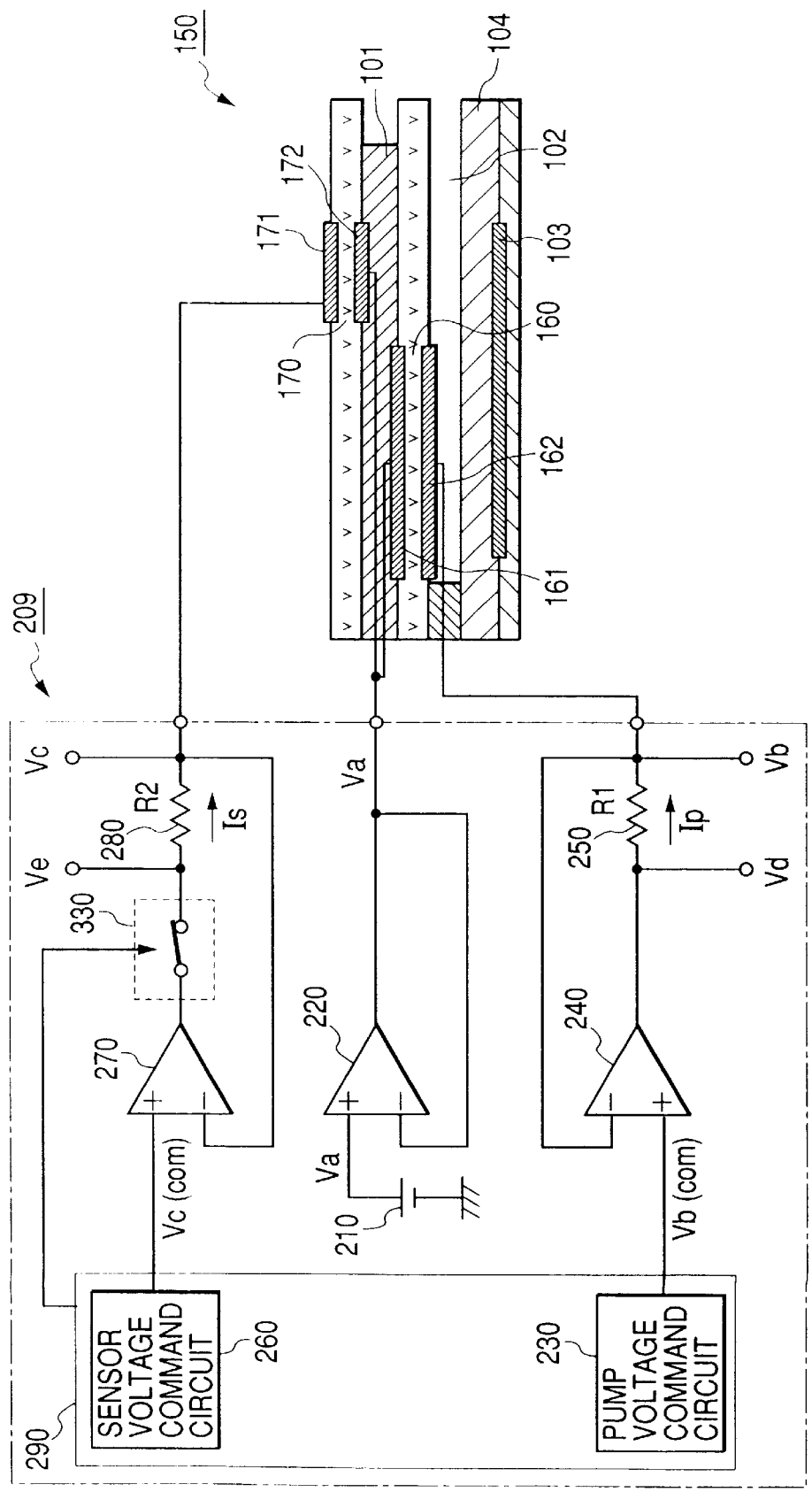
FIG. 27 is a diagram of a gas concentration sensing apparatus according to a twelfth embodiment of this invention.

FIG. 27 shows a twelfth embodiment of this invention which is similar to the tenth embodiment thereof except for design changes mentioned later. The embodiment of FIG. 27 includes a control circuit 209 which replaces the control circuit 201 in FIG. 14.

The control circuit 209 includes a switch circuit 330 interposed between a current sensing resistor 280 and the output terminal of an amplifier circuit 270. The switch circuit 330 is controlled by an applied voltage command circuit 290 in the control circuit 209. The switch circuit 330 is normally closed. When a negative current flows through a pump cell 160, that is, when a gas concentration sensor 150 is exposed to an exhaust gas originating from a rich air-fuel mixture, the applied voltage command circuit 290 opens the switch circuit 330 to remove the voltage application from a sensor cell 170. As a result, the sensor cell 170 is prevented from interfering with the pump cell 160 in sensing action.

Figure 28:
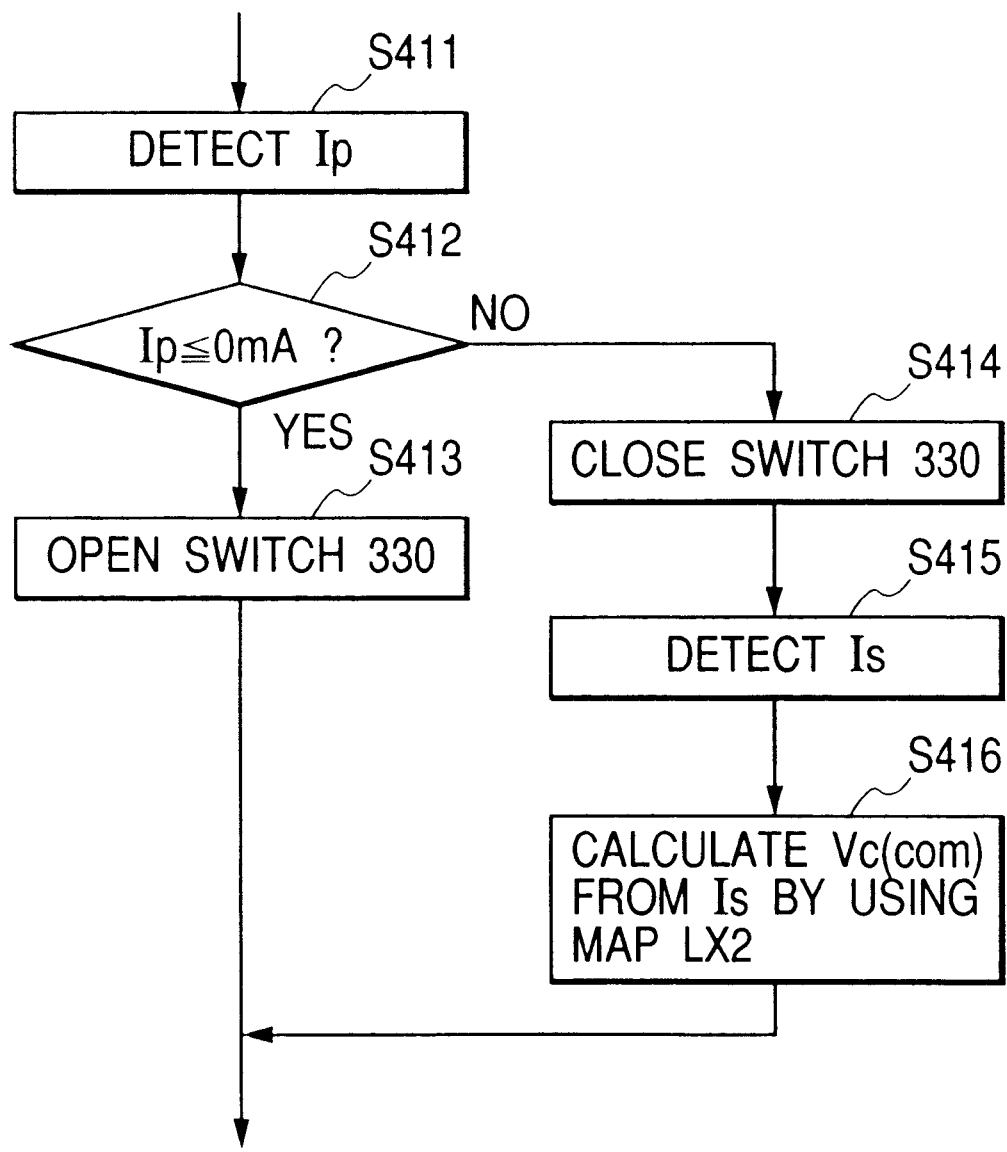
FIG. 28 is a flowchart of a portion of a subroutine of a control program for an applied voltage command circuit in FIG. 27.

FIG. 28 is a flowchart of a portion of a subroutine of a control program for the applied voltage command circuit 290 in the twelfth embodiment of this invention. As shown in FIG. 28, a step S411 calculates a pump cell current Ip according to an equation as "Ip=(Vd−Vb)/R1". A step S412 following the step S411 compares the detected pump cell current Ip with 0 μA to determine whether the detected pump cell current Ip is positive or negative. When the pump cell current Is is equal to 0 mA or is negative, the program advances from the step S412 to a step S413. The step S413 opens the switch circuit 330. As a result, the voltage application is removed from the sensor cell 170. In this case, a current hardly flows through the sensor cell 170, and the transfer of oxygen ($O_2$) from a porous diffusion layer 101 to an external space via the sensor cell 170 is forced to be suspended. After the step S413, the program advances to a next portion of the subroutine.

When the step S412 determines that the pump cell current Ip is positive, the program advances from the step S412 to a step S414. The step 414 closes the switch circuit 330 so that an effective voltage can be applied to the sensor cell 170. A step S415 following the step S414 calculates a sensor cell current Is according to an equation as "Is=(Ve−Vc)/R2". A step S416 subsequent to the step S415 calculates a target sensor command voltage Vc(com) from the sensor cell current Is by referring to the line LX2 in FIG. 6. After the step S416, the program advances to the next portion of the subroutine.

When the gas concentration sensor 150 is exposed to an exhaust gas originating from a rich air-fuel mixture, the step S413 opens the switch circuit 330 so that the transfer of oxygen ($O_2$) from the porous diffusion layer 101 to the external space via the sensor cell 170 is forced to be suspended. Accordingly, the sensor cell 170 is prevented from interfering with the pump cell 160 in sensing action.

Thirteenth Embodiment

Figure 29:
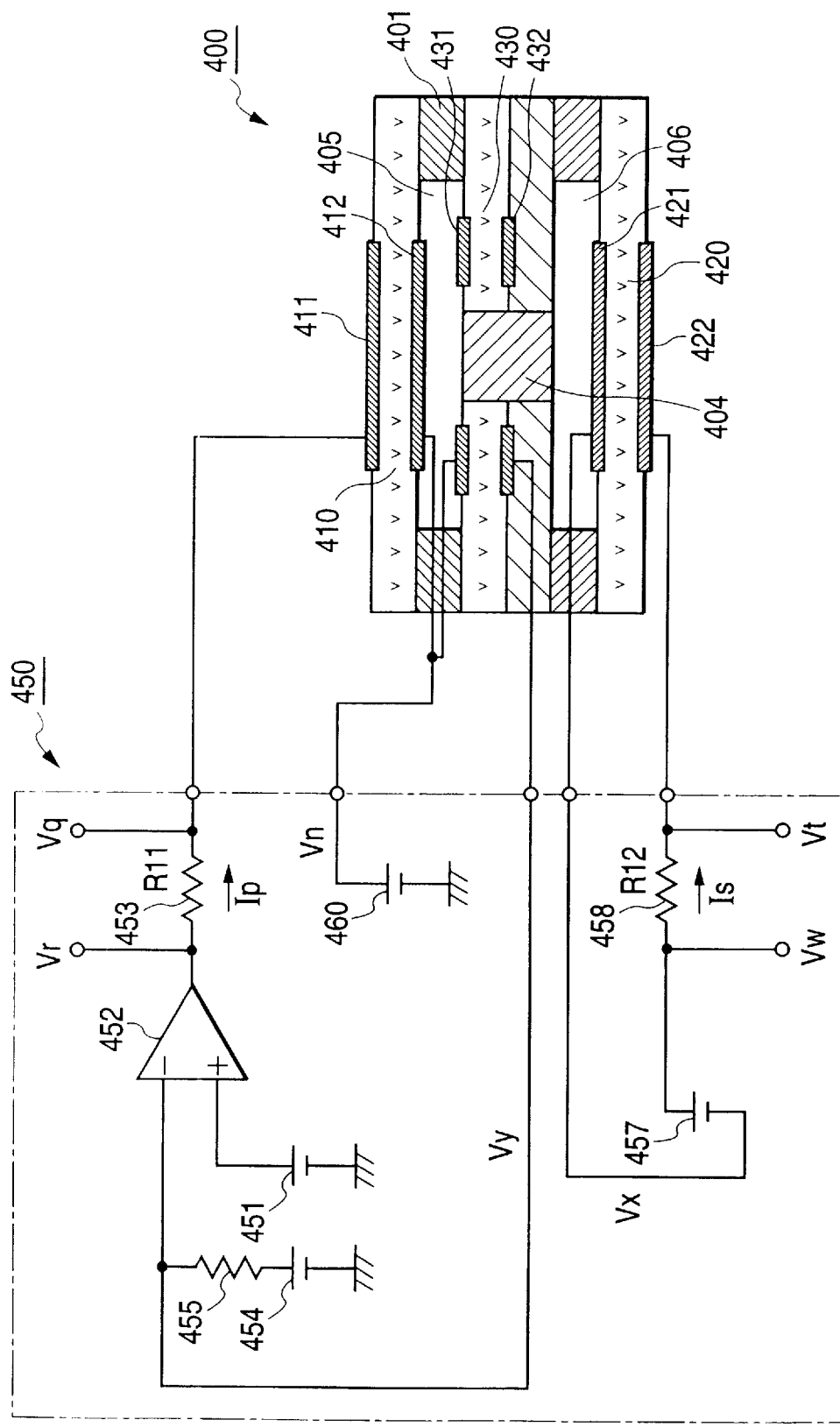
FIG. 29 is a diagram of a gas concentration sensing apparatus according to a thirteenth embodiment of this invention.

FIG. 29 shows a gas concentration sensing apparatus according to a thirteenth embodiment of this invention. The gas concentration sensing apparatus in FIG. 29 includes a gas concentration sensor 400 and a control circuit 450 which are connected to each other. Voltages derived from the voltage (12 V or 24 V) across an automotive battery are applied to the gas concentration sensor 400.

With reference to FIG. 29, the gas concentration sensor 400 includes a pump cell 410, a sensor cell 420, and a reference cell 430. The pump cell 410 acts to pump oxygen ($O_2$) from an exhaust gas. The pump cell 410 is used in detecting the oxygen ($O_2$) concentration in the exhaust gas. The sensor cell 420 acts to decompose NOx in the exhaust gas through a reaction as "NOx→(1/2)$N_2$+(x/2)$O_2$". Thus, the decomposition of NOx causes new oxygen ($O_2$). The sensor cell 420 pumps the new oxygen ($O_2$). The sensor cell 420 is used in detecting the NOx concentration in the exhaust gas. The reference cell 430 is used in detecting the partial pressure of oxygen ($O_2$) in the exhaust gas.

The gas concentration sensor 400 includes a first porous diffusion layer 401, and a first chamber 405 located between the pump cell 410 and the reference cell 430. An exhaust gas emitted from engine combustion chambers enters the first chamber 405 via the first porous diffusion layer 401. The reference cell 430 has a first electrode 431 and a second electrode 432. The first electrode 431 is exposed to the first chamber 405. A voltage between the first electrode 431 and the second electrode 432 of the reference cell 430 is fed to the control circuit 450. The pump cell 410 is controlled by the control circuit 450 in response to the voltage between the first electrode 431 and the second electrode 432 of the reference cell 430. The pump cell 410 has a first electrode 411 and a second electrode 412. The first electrode 411 is exposed to an external space. The second electrode 412 is exposed to the first chamber 405. The control circuit 450 applies an effective voltage between the first pump electrode 411 and the second pump electrode 412 so that the pump cell 410 will pump oxygen ($O_2$) from the exhaust gas in the first chamber 405 to the external space. The oxygen ($O_2$) concentration in the exhaust gas is detected from a current flowing through the pump cell 410.

The gas concentration sensor 400 includes a second porous diffusion layer 404 and a second chamber 406. The second chamber 406 is used as a reference gas chamber. The second porous diffusion layer 404 extends between the first chamber 405 and the second chamber 406. The exhaust gas from which oxygen ($O_2$) has been pumped flows from the first chamber 405 to the second chamber 406 via the second porous diffusion layer 404. The sensor cell 420 has a first electrode 421 and a second electrode 422. The first electrode 421 is exposed to the second chamber 406. The second electrode 422 is exposed to the external space. The control circuit 450 applies an effective voltage between the first sensor electrode 421 and the second sensor electrode 422 so that the sensor cell 420 will decompose NOx in the exhaust gas in the second chamber 406 through a reaction as "NOx→(1/2)$N_2$+(x/2)$O_2$". Thus, the decomposition of NOx causes new oxygen ($O_2$). The sensor cell 420 pumps the new oxygen ($O_2$) from the second chamber 406 to the external space. The NOx concentration in the exhaust gas is detected from a current flowing through the sensor cell 420.

The control circuit 450 includes a reference voltage circuit 460 for generating a predetermined reference voltage Vn higher than a ground potential. The positive terminal of the reference voltage circuit 460 is connected to the second electrode 412 of the pump cell 410 and the first electrode 431 of the reference cell 430. The negative terminal of the reference voltage circuit 460 is grounded. The second electrode 412 of the pump cell 410 and the first electrode 431 of the reference cell 430 are subjected to the reference voltage Vn higher than the ground potential.

The control circuit 450 includes an amplifier circuit 452 for controlling the pump cell 410. The second electrode 432 of the reference cell 430 is connected to the inverting input terminal of the amplifier circuit 452. Thus, the voltage Vy at the second electrode 432 of the reference cell 430 is applied to the inverting input terminal of the amplifier circuit 452. The control circuit 450 includes a dc power source 454 for generating a predetermined constant voltage. The positive terminal of the dc power source 454 is connected via a resistor 455 to the junction between the inverting input terminal of the amplifier circuit 452 and the second electrode 432 of the reference cell 430. The negative terminal of the dc power source 454 is grounded. The dc power source 454 causes a current through the reference cell 430, and thereby the reference cell 430 provides a constant oxygen ($O_2$) concentration. The non-inverting input terminal of the amplifier circuit 452 is connected to the positive terminal of a dc power source 451 for generating a predetermined reference voltage. The negative terminal of the dc power source 451 is grounded. The output terminal of the amplifier circuit 452 is connected via a current sensing resistor 453 to the first electrode 411 of the pump cell 410. The amplifier circuit 452 controls a pump cell applied voltage (that is, a voltage applied to the pump cell 410) in response to the voltage Vy at the second electrode 432 of the reference cell 430. The resistor 453 is used in sensing a current Ip flowing through the sensor cell 410. The sensor cell current Ip depends on the oxygen ($O_2$) concentration in the exhaust gas.

As an air-fuel mixture causing the exhaust gas in the first chamber 405 is leaner, that is, as the oxygen ($O_2$) concentration in the exhaust gas in the first chamber 405 is higher, an electromotive force by the reference cell 430 decreases so that the voltage Vy at the second electrode 432 of the reference cell 430 drops. The output voltage Vr of the amplifier circuit 452 and also the voltage Vq applied to the first electrode 411 of the pump cell 410 rise in accordance with the drop in the voltage Vy. The pump cell current Ip increases as the voltage Vq applied to the first electrode 411 of the pump cell 410 rises. Thus, the pump cell current Ip increases in accordance with the degree of the leanness of an air-fuel mixture causing the exhaust gas in the first chamber 405, that is, the oxygen ($O_2$) concentration in the exhaust gas in the first chamber 405. The pump cell 410 pumps oxygen ($O_2$) from the first chamber 405 to the external space. The pump cell current Ip is expressed as follows.

$$Ip=(Vr-Vq)/R11$$

where Vr and Vq denote the voltages at the opposite ends of the current sensing resistor 453 respectively, and R11 denotes the resistance of the resistor 453. The oxygen ($O_2$) concentration in the exhaust gas is detected from the pump cell current Ip or the voltage difference (Vr−Vq).

As previously mentioned, the exhaust gas from which oxygen ($O_2$) has been pumped flows from the first chamber 405 to the second chamber 406 via the second porous diffusion layer 404. The control circuit 450 includes a dc power source 457 for applying an effective voltage to the sensor cell 420. The first electrode 421 of the sensor cell 420 is connected to the negative terminal of the dc power source 457. The second electrode 422 of the sensor cell 420 is connected via a current sensing resistor 458 to the positive terminal of the dc power source 457. The dc power source 457 applies an effective voltage to the sensor cell 420, thereby activating the sensor cell 420. The sensor cell 420 decomposes NOx in the exhaust gas in the second chamber 406 through a reaction as "NOx→(1/2)$N_2$+(x/2)$O_2$". Thus, the decomposition of NOx causes new oxygen ($O_2$). The sensor cell 420 pumps the new oxygen ($O_2$) from the second chamber 406 to the external space. Generally, a current Is flowing through the sensor cell 420 depends on the NOx concentration in the exhaust gas. The sensor cell current Is is expressed as follows.

$$Is=(Vw-Vt)/R12$$

where Vw and Vt denote the voltages at the opposite ends of the current sensing resistor 458 respectively, and R12 denotes the resistance of the resistor 458. The NOx concentration in the exhaust gas is detected from the sensor cell current Is or the voltage difference (Vw−Vt).

Since the reference voltage Vn (that is, the voltage at the second electrode 412 of the pump cell 410 and the first electrode 431 of the reference cell 430) is higher than the ground potential, negative currents can be made to flow through the pump cell 410 and the reference cell 430 respectively. For not only an exhaust gas originating from a lean air-fuel mixture but also an exhaust gas originating from a rich air-fuel mixture, a gas component concentration in the exhaust gas in the first chamber 405 can be maintained at a constant level (for example, an oxygen ($O_2$) concentration in the exhaust gas in the first chamber 405 can be maintained in a stoichiometric state). Thus, it is possible to detect not only the air-to-fuel ratio (A/F) of a lean air-fuel mixture causing the exhaust gas but also the air-to-fuel ratio (A/F) of a rich air-fuel mixture causing the exhaust gas. Accordingly, a wide A/F sensible range is available. Furthermore, it is possible to provide an improved sensing response characteristic when an exhaust gas caused by a rich air-fuel mixture is replaced by an exhaust gas originating from a lean air-fuel mixture.

Fourteenth Embodiment

A fourteenth embodiment of this invention is a combination of the thirteenth embodiment thereof and one of the third to the twelfth embodiments thereof.

Fifteenth Embodiment

A fifteenth embodiment of this invention is a modification of one of the first to the twelfth embodiments thereof. In the fifteenth embodiment of this invention, an applied voltage command circuit 290 includes a pump voltage command circuit 230 and a sensor voltage command circuit 260 which are similar in design to each other.

Figure 30:
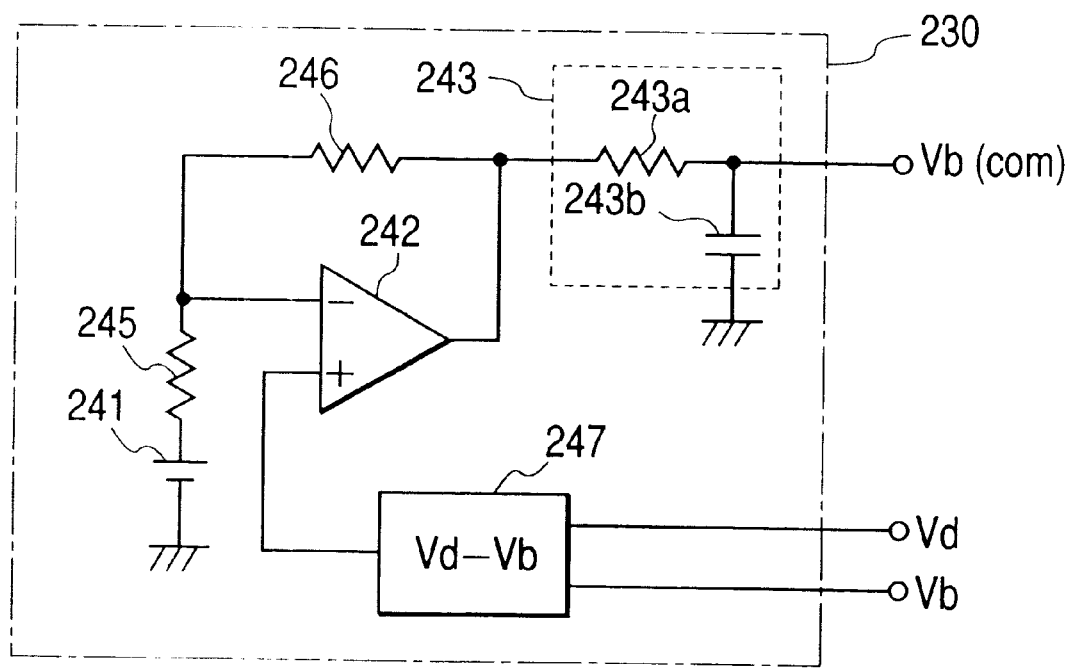
FIG. 30 is a diagram of a pump voltage command circuit in a fifteenth embodiment of this invention.

FIG. 30 shows the pump voltage command circuit 230 in the fifteenth embodiment of this invention. As shown in FIG. 30, the pump voltage command circuit 230 includes a reference voltage circuit 241, an amplifier circuit 242, resistors 245 and 246, a low pass filter 243, and a current detection circuit 247.

The current detection circuit 247 receives voltages Vd and Vb which appear at the opposite ends of a current sensing resistor 250 (see FIG. 9). The current detection circuit 247 generates a difference voltage (Vd−Vb). The current detection circuit 247 applies the difference voltage (Vd−Vb) to the non-inverting input terminal of the amplifier circuit 242. The inverting input terminal of the amplifier circuit 242 is connected via the resistor 246 to the output terminal thereof. Also, the inverting input terminal of the amplifier circuit 242 is connected via the resistor 245 to the positive terminal of the reference voltage circuit 241. The negative terminal of the reference voltage circuit 241 is grounded. The resistors 245 and 246 determine the amplification factor of the amplification circuit 242. The low pass filter 243 is connected to the output terminal of the amplifier circuit 242. The low pass filter 243 has a combination of a resistor 243a and a capacitor 243b. The amplifier circuit 242 generates a pump command voltage Vb(com). The amplifier circuit 242 outputs the pump command voltage Vb(com) to the low pass filter 243. The pump command voltage Vb(com) is transmitted to an external through the low pass filter 243.

A voltage corresponding to the line LX1 in FIG. 5 is applied to a pump cell 110 (see FIG. 9). The reference voltage circuit 241 provides an offset voltage corresponding to the line LX1 in FIG. 5. The offset voltage is equal to a pump cell applied voltage which occurs when a pump cell current is null. The amplifier circuit 242 and the resistors 245 and 246 determine a parameter corresponding the slope of the line LX1 in FIG. 5, that is, a rate of an increase in the pump cell applied voltage in response to an increase in the pump cell current.

The pump voltage command circuit 230 forms a portion of a feedback loop. The low pass filter 243 interposed in the feedback loop prevents oscillation from occurring therein.

Sixteenth Embodiment

A sixteenth embodiment of this invention is similar to the first embodiment thereof except for the following design change. In the sixteenth embodiment of this invention, the second electrode 112 of the pump cell 110 (see FIG. 9) is grounded.

Seventeenth Embodiment

A seventeenth embodiment of this invention is similar to the second embodiment thereof except for the following design change. In the seventeenth embodiment of this invention, the second electrode 172 of the sensor cell 170 (see FIG. 14) is grounded.

Eighteenth Embodiment

An eighteenth embodiment of this invention is similar to one of the first to the seventeenth embodiments thereof except that the gas concentration sensor 100, 150, or 400 is replaced by a gas concentration sensor of another type.

The gas concentration sensor in the eighteenth embodiment of this invention includes a first cell (a pump cell) and a second cell (a sensor cell). The first cell is opposed to a diffusion layer for introducing a measurement gas. An effective voltage is applied to the first cell, and thereby the first cell is activated. The first cell pumps oxygen ($O_2$) from the measurement gas. A current flowing through the first cell depends on the oxygen ($O_2$) concentration in the measurement gas. The second cell is opposed to the diffusion layer. An effective voltage is applied to the second cell, and thereby the second cell is activated. A current flowing through the second cell depends on the concentration of a specific component of the measurement gas from which oxygen ($O_2$) has been pumped. At least one of the first and second cells faces a reference gas chamber.

Nineteenth Embodiment

A nineteenth embodiment of this invention is similar to one of the first to the seventeenth embodiments thereof except that a member having a slit or a through hole replaces the porous diffusion layer for introducing the exhaust gas (the measurement gas).

Twentieth Embodiment

A twentieth embodiment of this invention is similar to one of the first to the seventeenth embodiments thereof except that the gas concentration sensor 100, 150, or 400 is replaced by a gas concentration sensor of another type.

The gas concentration sensor in the twentieth embodiment of this invention includes a pump cell and a sensor cell. The pump cell acts to pump oxygen ($O_2$) from an exhaust gas (a measurement gas). The pump cell senses the oxygen ($O_2$) concentration in the exhaust gas. The sensor cell decomposes HC or CO in the exhaust gas from which oxygen ($O_2$) has been pumped. The sensor cell senses the HC concentration or the CO concentration in the exhaust gas.

What is claimed is:

1. A gas concentration sensing apparatus comprising:

a gas introducing portion for introducing a measurement gas;

a first cell configured and disposed so as to be exposed to the measurement gas introduced via the gas introducing portion and configured to pump oxygen from the measurement gas in the gas introducing portion, the first cell comprising first and second first cell electrodes disposed on opposite sides of a first solid electrolytic layer;

a second cell configured and disposed so as to be exposed to the measurement gas introduced via the gas introducing portion and configured to sense a concentration of a specific component of the measurement gas from which oxygen has been pumped by the first cell, the second cell comprising first and second second cell electrodes disposed on opposite sides of a second solid electrolytic layer;

a reference gas chamber with respect to which one of the first and second cells is disposed such that the first electrode of said one of the first and second cells is exposed to a reference gas in the reference gas chamber and such that the second electrode of said one of the first and second cells is exposed to the measurement gas introduced via the gas introducing portion; and means for maintaining a voltage at the second electrode of said one of said first and second cells at a level greater than 0 V such that oxygen can be caused to be introduced into the gas introducing portion by means of said one of said first and second cells.

2. A gas concentration sensing apparatus as recited in claim 1, wherein the means for maintaining a voltage comprises means for applying a predetermined reference voltage to the second electrode of said one of said first and second cells, the predetermined reference voltage being greater, with respect to ground, than the voltages which are applied to the first electrodes of the first and second cells when the measurement gas lacks oxygen are, with respect to ground.

3. A gas concentration sensing apparatus as recited in claim 1, further comprising means for detecting an impedance of the first cell and means for detecting an impedance of the second cell.

4. A gas concentration sensing apparatus as recited in claim 1, wherein the measurement gas includes an exhaust gas and wherein said one of said first and second cells is said second cell, said gas concentration sensing apparatus further comprising a switch circuit interposed in a voltage feed path to the first electrode of the first cell and means for opening the switch circuit to suspend transfer of oxygen via the first cell when the exhaust gas is caused by a rich air-fuel mixture.

5. A gas concentration sensing apparatus as recited in claim 1, further comprising:
    means for sensing a current flowing through the first cell;
    means for applying a voltage to the first electrode of the first cell in response to the sensed current through the first cell;
    means for sensing a current flowing through the second cell; and
    means for applying a voltage to the first electrode of the second cell in response to the sensed current through the second cell.

6. A gas concentration sensing apparatus as recited in claim 5, further comprising a single power supply and means for deriving the voltages applied to the first electrode of the first and second cells from the single power supply.

7. A gas concentration sensing apparatus as recited in claim 5, further comprising an automotive battery and means for deriving the voltages applied to the first electrode of the first and second cells from the automotive battery, the measurement gas including an automotive exhaust gas.

8. A gas concentration sensing apparatus as recited in claim 5, wherein the means for sensing the current through the first cell includes a first current sensing resistor and means for detecting a voltage drop across the first current sensing resistor, and wherein the means for sensing the current through the second cell includes a second current sensing resistor and means for detecting a voltage drop across the second current sensing resistor.

9. A gas concentration sensing apparatus as recited in claim 5, wherein the measurement gas includes an exhaust gas and wherein said one of said first and second cells is said second cell, said gas concentration sensing apparatus further comprising means for controlling the voltage applied to the first electrode of the first cell to suspend transfer of oxygen via the first cell when the exhaust gas is caused by a rich air-fuel mixture.

10. A gas concentration sensing apparatus comprising:
    a gas introducing portion for introducing a measurement gas;
    a first cell configured and disposed so as to be exposed to the measurement gas introduced via the gas introducing portion and configured to pump oxygen from the measurement gas in the gas introducing portion, the first cell comprising a positive-side first cell electrode and a negative-side first cell electrode disposed on opposite sides of a first solid electrolytic layer;
    a second cell configured and disposed so as to be exposed to the measurement gas introduced via the gas introducing portion and configured to sense a concentration of a specific component of the measurement gas from which oxygen has been pumped by the first cell, the second cell comprising a positive-side second cell electrode and a negative-side second cell electrode disposed on opposite sides of a second cell solid electrolytic layer; and
    means for maintaining a voltage at each of the negative-side electrodes of the first and second cells at a level greater than 0 V such that oxygen can be caused to be introduced into the gas introducing portion by means of one of said first and second cells.

11. A gas concentration sensing apparatus as recited in claim 10, further comprising:
    means for sensing a current flowing through the first cell;
    means for applying a voltage to the positive-side electrode of the first cell in response to the sensed current through the first cell;
    means for sensing a current flowing through the second cell; and
    means for applying a voltage to the positive-side electrode of the second cell in response to the sensed current through the second cell.

12. A gas concentration sensing apparatus as recited in claim 11, further comprising a single power supply and means for deriving the voltages applied to the positive-side electrode of the first and second cells from the single power supply.

13. A gas concentration sensing apparatus as recited in claim 11, further comprising an automotive battery and means for deriving the voltages applied to the positive-side electrode of the first and second cells from the automotive battery, the measurement gas including an automotive exhaust gas.

14. A gas concentration sensing apparatus as recited in claim 11, wherein the means for sensing the current through the first cell includes a first current sensing resistor and means for detecting a voltage drop across the first current sensing resistor, and wherein the means for sensing the current through the second cell includes a second current sensing resistor and means for detecting a voltage drop across the second current sensing resistor.

15. A gas concentration sensing apparatus as recited in claim 11, wherein the measurement gas includes an exhaust gas and wherein said one of said first and second cells is said second cell, said gas concentration sensing apparatus further comprising means for controlling the voltage applied to the positive-side electrode of the first cell to suspend transfer of oxygen via the first cell when the exhaust gas is caused by a rich air-fuel mixture.

16. A gas concentration sensing apparatus as recited in claim 10, further comprising means for detecting an impedance of the first cell and means for detecting an impedance of the second cell.

17. A gas concentration sensing apparatus as recited in claim 10, wherein the measurement gas includes an exhaust gas and wherein said one of said first and second cells is said second cell, said gas concentration sensing apparatus further comprising a switch circuit interposed in a voltage feed path to the positive-side electrode of the first cell and means for opening the switch circuit to suspend transfer of oxygen via the first cell when the exhaust gas is caused by a rich air-fuel mixture.

18. An apparatus for sensing a concentration of NOx in a measurement exhaust gas, comprising:

first means for pumping $O_2$ from the measurement exhaust gas to change the measurement exhaust gas to a second exhaust gas in cases where the measurement exhaust gas is in a first state originating from a lean air-to-fuel mixture;

second means for generating an electric power;

third means receiving the electric power generated by the second means for decomposing NOx in the second exhaust gas and thereby generating new $O_2$, and for pumping the new $O_2$ from the second exhaust gas to a reference gas in response to the received electric power in cases where the measurement exhaust gas is in the first state;

fourth means for sensing an electric current flowing in the third means as an indication of a concentration of NOx in the measurement exhaust gas in cases where the measurement exhaust gas is in the first state;

fifth means for changing the electric power received by the third means from a first polarity to a second polarity opposite to the first polarity when the measurement exhaust gas changes from the first state to a second state originating from a rich air-to-fuel mixture;

sixth means for changing the electric power received by the third means from the second polarity to the first polarity when the measurement exhaust gas changes from the second state to the first state;

wherein the changes of the electric power between the first and second polarities by the fifth and sixth means enable the sensing of the NOx concentration to be quickly resumed after the measurement exhaust gas changes from the second state to the first state.

* * * * *